(12) United States Patent
Gao et al.

(10) Patent No.: US 7,544,793 B2
(45) Date of Patent: Jun. 9, 2009

(54) MAKING NUCLEIC ACID SEQUENCES IN PARALLEL AND USE

(76) Inventors: Xialoian Gao, 22128 Belefontaine, Houston, TX (US) 77030; Xiaochuan Zhou, 22128 Belefontaine, Houston, TX (US) 77030; Xiaolin Zhang, 5216 Meadow Landing La., Sugar Land, TX (US) 77479; Nuing Sheng, 5216 Meadow Landing La., Sugar Land, TX (US) 77479; Qi Zhu, 3831 N. Braeswood, Apt. 6, Houston, TX (US) 77025

( * ) Notice: Subject to any disclaimer, the term of this patent is extended or adjusted under 35 U.S.C. 154(b) by 0 days.

(21) Appl. No.: 11/365,980

(22) Filed: Mar. 1, 2006

(65) Prior Publication Data

US 2007/0031942 A1    Feb. 8, 2007

Related U.S. Application Data

(60) Provisional application No. 60/657,304, filed on Mar. 1, 2005.

(51) Int. Cl.
  *C07H 21/00* (2006.01)
(52) U.S. Cl. .................................................. 536/25.3
(58) Field of Classification Search ................... None
  See application file for complete search history.

(56) References Cited

U.S. PATENT DOCUMENTS 5,942,609 A * 8/1999 Hunkapiller et al. ....... 536/25.3
6,245,505 B1  6/2001 Todd
6,355,431 B1  3/2002 Chee
6,670,127 B2 * 12/2003 Evans ............................. 435/6
7,164,992 B1 * 1/2007 Mulligan et al. ............... 702/20
2003/0215825 A1 * 11/2003 Tong ............................. 435/6
2003/0219781 A1 * 11/2003 Frey .............................. 435/6
2006/0160138 A1 * 7/2006 Church et al. ................ 435/7.1

FOREIGN PATENT DOCUMENTS

WO   WO 2004/039953   *  5/2004

OTHER PUBLICATIONS

Barndad, Cynthia, "A DNA, Self-Assembled Monolayer for the Specific Attachment of Unmodified Double- or Single-Stranded DNA," Biophysical Journal, Oct. 1998, vol. 75, pp. 1997-2003.*
Zhou et al., "Microfluidic PicoArray synthesis of oligodeoxynucleotides and simultaneous assembling of multiple DNA sequences," Nucleic Acids Research, vol. 32, No. 18, pp. 5409-5417.*
Sarkar, et al. Nucleic Acids Res. 2005. vol. 33, No. 1, pp. 143-151.

* cited by examiner

*Primary Examiner*—Kenneth R. Horlick
*Assistant Examiner*—Molly E Baughman
(74) *Attorney, Agent, or Firm*—G Kenneth Smith; Pat Halloran

(57) ABSTRACT

The present invention relates generally to the fields of genomics, synthetic biology and genetic engineering. More particularly, the present invention concerns the methods that enable parallel multiplex ligation and amplification on surface for making assemblies of nucleic acids of various biological applications and for analysis of biological samples such as DNA, RNA, and proteins.

3 Claims, 21 Drawing Sheets

Figure 1A-E

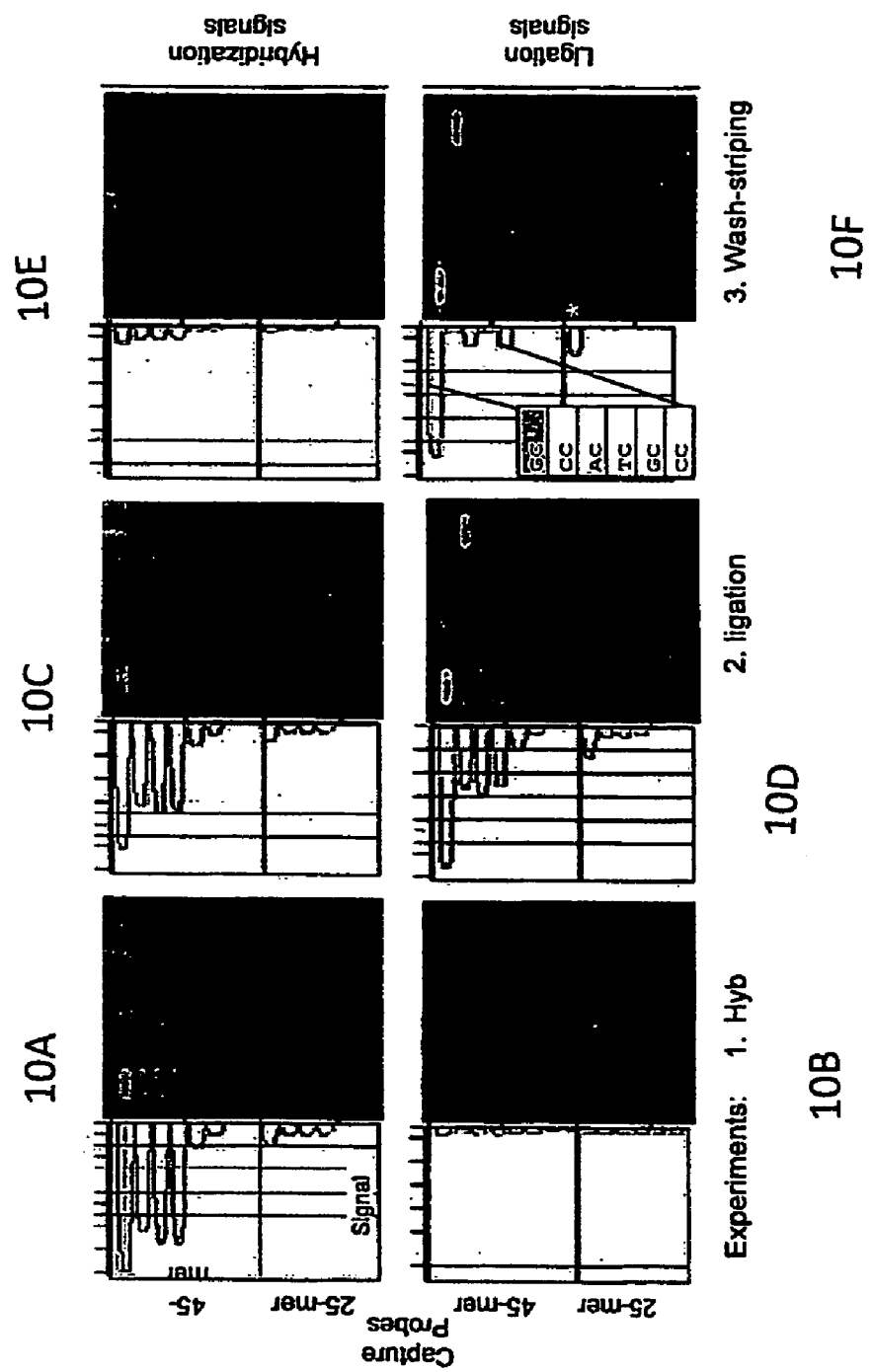
Figure 10A-F

MAKING NUCLEIC ACID SEQUENCES IN PARALLEL AND USE

RELATED APPLICATIONS

This application claims priority to U.S Ser. No. 60/657,304 filed Mar. 1, 2005.

Field of the invention

The present invention relates generally to the fields of genomics, synthetic biology and genetic engineering. More particularly, the present invention concerns the methods that enable parallel multiplex ligation and amplification on surface for making assemblies of nucleic acids of various biological applications and for analysis of biological samples such as DNA, RNA, and proteins.

Description of Related Art

This invention relates to the fields of nucleic acid technologies, specifically to the preparation and application of nucleic acids of predetermined sequences and their use. Increasingly, research and applications at genomic scale based on fundamental molecular sciences dominate the major advancement of biosciences and technologies. As the scope of the problems to be investigated is quickly expanding, there must be tools available for faster, cheaper, and better experiments. Dramatic progress has been made in the transition from traditional molecular biological techniques to miniaturization, parallelization, and automation in investigating problems at genomic and proteomic scales. Traditional single experiments are now performed on 96- or 384-well plates in parallel using liquid handling robotics. These experiments use micromols (µmol) of materials and milliliters (ml) of solutions. However, the present level of advancement is limited in large-scale applications, such as those at the genome-scale or involving large sample sets. This is because such a large-scale experiment would require thousands to millions of tests. The consequence is extremely costly material preparation taking a very long period of time (months to years). One such example is genome-wide single nucleotide polymorphism (SNP) analysis based on a large population. Such an experiment would provide invaluable information for genetic prediction and prevention of hereditary diseases and for molecular diagnostics of life-threatening diseases, such as cancers. If a single experiment per SNP per person uses ten milliliter (10 ml) of solution, the overall experiment for, for instance, 100,000 SNP and 1,000 people, would then consume, for solvents alone, 1,000,000 liters (l), equivalent to the annual capacity of a small chemical plant. Another example that demonstrates the inadequacy of the current methods is preparation of synthetic genes from synthetic oligodeoxyribonucleotides (oligos) for genome assemblies. A small genome usually contains approximately five million base pairs (bps) which would include several thousand genes. For the solvent alone, the conventional methods of oligo preparation would consume 50,000 l or more assuming 5 ml solvent consumption per synthesis cycle. Clearly, at this level of material consumption, it is not practical to conduct research and development at a genome-scale. For these large-scale experiments, a massive amount of instruments and ample spaces would be required for handling and storing of these reagents. The overall process would be laborious, time consuming, and error-prone. To overcome these problems, it is desirable to development technologies that reduce the consumption of reagent from µmol (solid) or ml (liquid) by a factor of 1,000 or more. The advantages for such technologies are evident and would enable genome-scale experiments, accelerate the understanding of complex biology of cellular systems, and permit discovery of novel regulatory mechanisms and saving of natural resources. The saving in material consumption and time also translates into environmental friendly and economic sensible process.

Synthesis of large DNA fragments which may be partial or complete gene sequences, any part of chromosomal DNA or DNA of biological sources, or any arbitrary sequences is one goal of the present invention. DNA sequence information and powerful computational methods now make it possible to engineer DNA sequences. These sequences can simulate or alter the functions and roles of a large number of transcribed RNA and translated proteins. This emerging field, called synthetic biology, encompasses the creation of DNA libraries for transcription of RNA sequences and for expression of proteins/antibodies and peptides which can provide biomedical, agricultural, and environmental benefits. Synthetic biology also involves the construction of entire genomes for making RNA and proteins, which can then be assembled to form biomolecular complexes, biological pathway systems, organisms, and cells. The current methods of DNA synthesis are too expensive and too slow for assembling long nucleic acid molecules from oligos or restricted to natural DNA sequences through assemblage of shuffled digested DNA fragments (Stemmer, 1994).

DNA synthesis using oligos has been used by molecular biologists for making natural genes, mutated genes (truncation, fusion, insertion/deletion), hybrid genes, transgenic genes, etc. (Dillon et al., 1990; Stemmer et al., 1995; Au et al., 1998). Synthetic genes, which often have lengths of one thousand base pairs (1 kbp) or greater, have traditionally been assembled one at a time by joining oligos of 30-80 bps in solution as a pool of mixture sequences. The oligos are specially designed according to the sequence of the DNA to be assembled and chemically synthesized on solid support, such as controlled porous glass (CPG), and the oligos are assembled to form long DNA usually without purification. The gene assembling process accomplishes two tasks: (1) annealing or hybridization of oligos to form a duplex and (2) ligation to join these oligos to form a long chain of covalently linked nucleotides. Alternatively, oligo duplexes containing overlapping regions can be extended into long chain products by the polymerase chain reaction (PCR). Present methods of gene synthesis may differ in order of the hybridization, ligation and/or PCR steps but all have the same limitations with respect to scalability. One current synthesis method is to design a set of oligos according to the DNA of interest and combine ligation and PCR in the same process, (e.g. ligation chain reaction (LCR)), which uses a pool of oligos and both DNA ligation and extension enzymes. This process generates DNA fragments of intermediate lengths and these fragments are subsequently joined as the full length DNA using overlapping PCR. This method has been used to produce a synthetic 5.4 kbp phage (Smith et al., 2003) and a 7.5 kbp polioviral genome (Cello et al., 2002). Another method (U.S. Pat. Nos. 6,521,427 and U.S. Pat. No. 6,670,127) of synthesizing a double-stranded polynucleotide includes annealing a terminus duplex which is sequentially annealed to another oligo and this annealing step is serially repeated to produce a double stranded long DNA. The nicks between the annealed oligos in the duplex are ligated. Overall, the current methods of DNA synthesis produce a single sequence per assembling reaction and thus are slow and expensive.

Oligonucleotide synthesis, historically, was not developed for large-scale parallel applications but rather for applications requiring individual sequences. Today it is still accomplished essentially on a one-by-one basis. Current methods of high throughput synthesis are limited to about 40,000 bp/day and costs about $0.10/bp. Thus, preparing the oligos for assembling a small genome of 5,000 genes of about 1,000 kbp per gene (5M bps) would take $0.5 M and 125 days (counting 24 h/day of operating time). For the gene synthesis, the total number of 40-mer oligos required is 250,000. The oligos would be individually collected, brought to a required concentration, and then pooled according to the gene synthesized. A laboratory would need to depend on liquid handling robotic instruments and large temperature-controlled storage spaces, making the overall process even more time consuming and costly. Since the pooled oligos are prone to operator errors and may have different concentrations, the deficiency of one oligo in an assembly could cause synthesis of the entire gene to fail. Under these sub-optimal conditions, a single synthetic gene would cost about $2.00 per base pair and could require four weeks for the overall synthesis.

Recent advancement in DNA oligo synthesis on microchips has greatly increased the throughput of oligo synthesis (Zhou et al. 2004). In this method, thousands of oligos were synthesized in parallel in a microfluidic device containing thousands of individual tiny reaction chambers. Each of the reaction chambers has picoliter (pL) volume and oligos synthesized in these chambers are collected after cleavage from the surface as a mixture. The microchip-based synthesis of thousands of oligos consumes the same amount as that of the materials normally for the synthesis of one oligo. The resultant oligo mixture is handled in a microtube, and thus significantly simplifies the process for use of the oligo mixture, such as gene synthesis. This microchip oligo mixture approach was used to construct a full-length green fluorescent protein (GFP) gene 714 bp in length by ligation (Zhou et al. 2004). Alternatively, a method using separate PCR reactions of the oligo mixture followed by removal of the primer sequences through restriction enzyme cleavage and overlapping PCR of the amplified oligo duplexes produced 21 genes encoding *E. coli* 30S ribosomal proteins, in total of 14.6 kbps in length (Tian et al 2004). Purification by hybridization of the amplified oligos resulted in a nine fold enhancement of fidelity (Tian et al. 2004).

The method of gene synthesis described above overcomes some of the problems associated with slow and expensive oligo synthesis but it is still not suitable for simultaneous assembling of a large number of genes or DNA fragments. The correct assembling of a full length gene or a DNA fragment requires the correct annealing of its component oligos. These oligos are usually 30-50 residue long and thus for a 1 kbp duplex, more than 40 oligos are required. This is a high order reaction of n components (n=number of oligos) and the chance of failure in full length gene assembly is depending on the size of "n". When n=40 or greater, the change of failure is high. In high throughput gene synthesis, multiple genes, and thus hundreds or more oligos are to be assembled simultaneously. Since oligos there are highly cross reactive in inter-strand base pairing and formation of intra-strand structures, the chances of gene synthesis failure due to the high order reaction and oligo cross interactions dramatically increase as n increases. There are no examples of simultaneous assembling of more than ten genes or long DNA fragments.

Several enzymatic reactions are useful for making long nucleic acids, which including ligation, gap filling (where gap filling may be part of the ligation reaction), chain extension, and PCR. Ligation reaction involves ligation enzymes, ligases, such as DNA ligases: Taq ligase, T4 ligase, and T7 ligase, and RNA ligases: T4 RNA ligase, which joins the 5'-phosphate and the 3'-OH of oligos together by forming a phosphodiester internucleotide bond. In one form of ligation, single stranded nucleic acid sequences or blunt end duplexes are ligated. In another form of ligation, the joining oligos (ligation oligos) are hybridized to a complementary strand (template strand) to form a duplex containing nicking sites and thus the 5'-phosphate and the 3'-OH groups are positioned in close proximity and ligated. In yet another form of ligation, two or more duplexes of a pair partial overlapping oligos hybridize to form a duplex containing consecutive overlapping oligo pairs of adhesive ends. The duplex contains two or more nicking sites and thus the 5'-phosphate and the 3'-OH groups are positioned in close proximity and ligated. In the ligation of duplex forms, the efficiency of the ligation reactions is determined by the complementary base pair (A pairing to T and C pairing to G) of both ligation oligos to the template strand, since ligation is favored by a stable duplex structure at the enzyme reaction site. This base pairing requirement has been explored in detection of specific genomic or RNA sequences and in DNA sequence variation analysis where the changes in sequence, such as an A to G mutation, can be detected by creating a ligation site at the mutation site and the formation of ligation product in the presence of a template strand containing a C but not a T at the site of mutation. These ligation-based methods have been widely used for SNP detection and haplotyping of human genome and for identification of specific genes in gene expression profiling (Landegren et al. 1988; Nickerson et al. 1990; Bibikova et al. 2004; Fan et al. 2004). These applications have a general theme which is to perform ligation in solution in the presence of a template strand followed by the detection of the ligation products through their hybridization to probes on surface and fluorescence, chemical luminescence, or other types of detectable signal readings. An alternative method to solution ligation is a ligation on the surface of optical thin film biosensor arrays by attaching sequence specific probes, which correspond to a genotype (Zhong et al. 2003). This experiment demonstrated the positive ligation of the correct genotype using perfectly matched oligos. The advantage of the ligation-based genetic analysis is enhanced sequence specificity compared to hybridization-based genetic analysis. These methods require pre-synthesized oligos, and thus large-scale experiments suffer from the same limitation as discussed for oligo-based large DNA synthesis.

Oligo-based applications, such as gene synthesis and ligation for detection and quantitation of genetic analysis, are affected by the quality of oligos used. Impure oligos are those that contain incorrect sequences and/or incorrect lengths. These impure oligos cause low fidelity gene synthesis, limit the lengths of DNA that can be synthesized, distort the quantity of analysis, and even produce false positive or false negative results. Although conventional oligo synthesis gives high stepwise yield which is in general greater than 98.5%, the misincorporation of nucleotides (substitution) as well as deletion and insertion are frequently observed at a rate as high as 1/160 bp (Tian et al. 2004). At such an error rate, long DNA (longer than 1 kbp) cannot be assembled at a sufficiently high efficiency. It would then demand large-scale sequencing in order to fish out the correct full length sequences among the many error-containing sequences. Although most of the prior methods of gene assembly have used oligos without purification, several methods have been shown for improving the quality of ligation-based applications: (a) Computer aided design of oligo sequences is used to minimize incorrect hybridization and to optimize the lengths, the sequence composition, the balanced duplex stability which is measured by melting temperature ($T_m$), and other physiochemical parameters of the oligos (Rouillard et al. 2003). (b) Affinity purification of oligos by hybridization to complementary strands (Zhou et al. 2004; Tian et al 2004) where ligation oligos hybridize to complementary strands immobilized on surface and the error-containing sequences are washed off since they form less stable duplexes. (c) Enzymatic recognition and/or digestion of error-containing DNA sequences such as endonuclease cleavage of mistmatch, bulge, and loop sequences. Examples of the enzymes that can recognize non-complementary nucleic acid duplexes include T7 endonuclease I, T4 endonuclease VII, mutS/mutY/mutL mismatch binding and repair proteins, and single strand binding proteins. (d) Chemical degradation of error-containing DNA sequences. Many organic and inorganic molecules bind and are capable of inducing cleavages in nucleic acids (Gao and Han, 2001). (e) Use of purification tag incorporated in the synthesis of oligos to separate correct from error oligos. Examples of the purification tags include biotin (binding to avidin or strepmtavidin), thiol (formation of disulfide bond and binding to gold), and other types of molecular moieties that allow the separation based on binding affinity, charge, or size between the correct and error-containing oligos. (f) Chromatography separation of the correct and error-containing sequences such as DHPLC (Mulligan and Tabone (2003) U.S. Pat. No. 6,664, 112).

There are many applications involving the use of synthetic DNAs, such as making RAN or defined sequences by in vitro transcription or protein or peptide libraries. Again, historically, the processes of generating these RNA transcripts or protein products by design from DNA of defined sequences are carried out in a manner of one at a time and thus the making of these biologically important molecules is slow and expensive. It is not a common practice to take advantage of ready-to-use synthetic RNA or protein molecules.

The methods of the present invention overcome the limitations of the prior art methods of gene assembly and provide fast, efficient and cost effective methods for producing one or more oligos or polynucleotides of desired lengths and sequences that can be used in a variety of applications.

SUMMARY OF THE INVENTION

The methods of the present invention relate to multiplexing enzymatic reactions on solid surface. In particular these reactions include, but are not limited to ligation, amplification, replication, transcription, and translation, and the reactions produce products that may be different from those before the reaction. The newly formed products may be used in the subsequent reactions performed again as multiplexing reactions. In some embodiments of the methods of the present invention the reactions may involve the use of a mixture of oligos of defined sequences (oligo mixture). For example the mixture of different oligonucleotides may be used in methods for generating longer nucleic acid molecules. The ligation, amplification, replication, transcription, and translation reactions are preferably performed in parallel at individual sites on a surface that has a reaction site density of at least nine sites per square millimeter (mm$^2$) but up to 2.0×10$^{11}$ sites per mm$^2$. The present invention describes methods of multiplexing reactions in tens, hundreds, thousands, ten thousands, hundred thousands, millions spatially separated reactions sites on surface.

In the methods of the present invention there is at least one type of oligonucleotide sequence and there may be multiple types of sequences per reaction site. In a preferred embodiment of the present invention, two or more sequences are anchored within the same individual reaction sites in a molecular vicinity fashion, wherein enzymatic reactions, such as ligation, take place between the sequences of molecular vicinities.

The present invention describes methods for parallel ligation using hybridization and ligation oligos of defined sequences as a oligo mixture on surface. Such ligation reactions accompanying or following hybridization provide improved specificity for genetic sequence analyses, such as detection of micro RNA (miRNA) sequences, SNP, and aberrant chromosomal arrangements, profiling gene expression, and sequencing.

Preferred embodiments of the present invention include methods in which the prescribed reactions occur inside isolatable reaction site(s). The isolation of the reaction sites may be in a microfluidic picoarray reaction device, by surface tension (Gao et al. 2001; Srivannavit et al. 2004), on distributed beads, on distributed nanoparticles, or as a single molecule array on solid surfaces.

In some other preferred embodiment of the present invention, methods are described for producing DNA, RNA, or DNA-RNA chimerias. Modified residues of nucleic acids are incorporated or post-modified by methods well known to those skilled in the field. Long DNA constructs which normally cannot be produced using chemical synthesis, such as DNA sequences of 100 bases and longer. The high throughput production of long DNA constructs enable genome-scale experiments such as making synthetic genes for biosynthesis of libraries of DNA, RNA, proteins, antibodies, or peptides of biomedical, diagnostic, therapeutic importance. The DNA constructs of defined lengths and sequences, synthetic genes, and its transcription and translation products are materials for making microarrays of DNA fragments, cDNA, cRNA, peptides, and proteins. In some preferred embodiment of the present invention the synthesis of long DNA by ligation of oligos proceeds in a stepwise manner. As a matter of choice, the stepwise reaction can be monitored to validate the reaction and control the quality of the reaction.

In some preferred embodiment of the present invention, the ligation oligos as a mixture and the surface bound oligos (capture probes) are designed from the consecutive regions of DNA sequences. Capture probes are 5'-phosphorylated using chemical or enzymatic phosphorylation methods. Alternatively, 5'-phosphate for the capture probes may be generated by nuclease cleavage at the designated position. The ligation oligos and the capture probes are hybridized to template strands or self-annealing to form duplex containing nicking and/or gapping sites. Those incorrectly hybridized sequences are removed from surface by applying stringent hybridization conditions, such as raising temperature, reducing salt concentration, and/or adding denaturing reagents such as SDS, formamide, and/or DMSO. Such procedures improve hybridization specificity and result in high fidelity ligation products. In some preferred embodiment of the present invention, the synthetic sequences on surface are bound to proteins or ligand molecules that bind differently to complementary duplexes versus incorrectly hybridized sequences. The resultant complexes provide mechanism of separation of the two types of sequences and thus improve the quality of the synthetic sequences.

In the embodiment of the present invention, the ligation reaction involves direct ligation or a combination of gap-filing and ligation functions (gap-filling/ligation). The ligation requires 5'-phosphate group (5'-P) and 3'-OH at the junction of two nucleic acid sequences co-hybridized to a template strand of a nucleic acid sequence. Therefore, ligation is a controllable process by the presence of both 5'-P and 3'-OH. Modifications on these sites, such as removal, blocking, or substitution of 5'-P and/or 3'-OH, will inhibit ligation or gap-filling/ligation due to non-ligatable 5'- and/or 3'-ends of the oligo.

BRIEF DESCRIPTION OF THE FIGURES

FIG. 3C—A schematic illustration of the use of two different adjacent oligonucleotides and the target hybridization to a surface oligonucleotide and ligation on surface between target and the other oligonucleotide on surface. The procedure also produces duplexes. (g) A plurality of oligos in pairs on surface. The pair of sequences in antiparallel orientation with regard to the 5'-terminus and is at least partially a duplex. Target sequences of various lengths are hybridized to the surface probes (7a and 7b as hybridized duplexes or 7c and 7d as alternative hybridizing strands). (h) Performing ligation followed by (i) washing to produce ligated duplex sequences from those with the correct ligation alignment.

FIG. 4B—A schematic illustration of miRNA detection by multiple hybridization and ligation reactions on chip. X=(LNA)n, other modified nucleotides; n=0, 1, 2, 3, etc.; the size of n is preferablly selected to balance different melting temperatures of the hybridizing duplexes. Z=Am, other sequences which is complementary to X; m=1, 2, etc. to 100 residues. Nk=oligonucleotide; k=3, 4, 5 to 5,000 residues. N'k'=oligonucleotide which containing at least a region complementary to the ligation sequence; k'=3, 4, 5 to 5,000 residues. Circle is a detection tag as defined in the text. Similarly, capture probe can be in 5'-3' orientation, opposite to what is shown in the Figure. Wherein species 1a is the capture probe and 1b is the sample miRNA with poly(A) added to the 3'-tail. Wherein 2b and 2c are ligation sequences without or with a detection tag. Wherein 3a and 3b are hybridizing duplexes without or with a detection tag. Wherein 4a and 4b are ligated sequences without or with a detection tag; 4c is capture probe which does not have a complementary target sequence. Wherein 5 is representative of a hybridizing duplex formed through multiple steps of hybridization and ligation; where in the ligated oligos may be modified to contain detection tag or multiple detection tags.

DETAILED DESCRIPTION OF THE INVENTION

Definition

Figure 1:
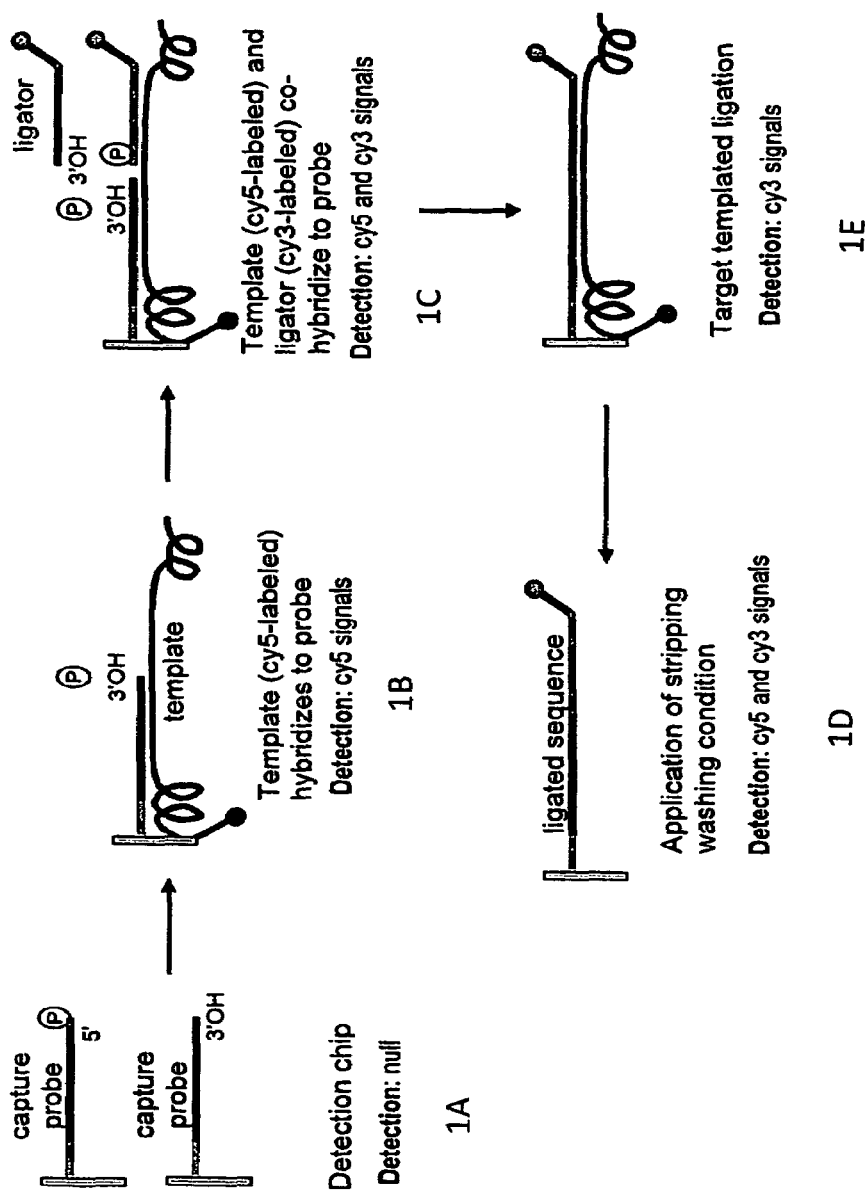
FIG. 1A-E—Illustration of the basic scheme or the hybridization-ligation process carried out on-surface. Surface linker and spacer of the capture porobe were not shown and the capture probes have 3'-OH or 5'-OPO$_3$ (5'-P) away from the surface. Hybridization with a template sequence which may be labeled with detection dye (the circle). The subsequent hybridization with a ligation oligo (ligator) sequence, which may also be labeled with detection dye (the circle). Ligation then results in linking two oligos on surface and the formation of a longer duplex; and removal of the hybridized template strand under stringent wash-stripping conditions to leave single stranded sequence.

The following terms are intended to have the following general meaning as they are used herein:

The term "substrate" and "surface", and "solid support" are used interchangeably to refer to any material that is suitable for derivatization with a functional group and for nucleic acid synthesis.

The term "nucleotide" refers to a compound comprised of a base linked to a pentose sugar through a glycosidic bond and a phosphate group at the 5'-position of the sugar. Natural nucleotides contain bases which are adenine (A), cytidine (C), guanine (G), thymine (T), and uridine (U).

The term "modified nucleotide" refers to a compound which contains chemical moieties that is different from or additional to those of natural nucleotides.

The term "linker" refers to an anchoring group that serves to anchor or tether a molecule to a solid support during solid phase synthesis.

The term "spacer" refers to a chemical group connected to a linker or an anchor moiety that is used to in between the linker and the immobilized nucleic acids or oligonucleotides and as a site for initiating synthesis of a polymer chain. Examples of spacer include, but are not limited to, ethyleneglycol polymer, alkyl, molecules containing branch side chains, dendrimers, oligonucleotides, peptides, peptditomimetics. Spacer molecules are sometimes terminated with hydroxyl or amino groups for synthesis of oligonucleotides or immobilization of nucleic acid sequences.

The term "3'-5' synthesis" refers to the addition of a 3'-phosphoramidite nucleotide to the 5'-OH end of a polynucleotide chain; 3'-5' synthesis is commonly used for oligonucleotide synthesis.

The term "5'-3'synthesis" refers to the addition of a 5'-phosphoramidite nucleotide to the 3'-OH end of a polynucleotide chain. The 5'-3'synthesis is also termed reverse synthesis.

The term "failure sequence" refers to the oligos obtained from a synthesis whose sequences are incorrect according to what are designed. The errors in failure sequences include deletion, insertion, and substitution of nucleotides, and the truncation of oligonucleotides.

The term "dye" refers to a molecule, compound, or substance that can provide an optically detectable signal (e.g., fluorescent, luminescent, calorimetric, topological, etc). For example, dyes include fluorescent molecules that can be associated with nucleic acid molecules.

The term "labeling" refers to a modification to nucleic acid and oligonucleotides which provides signals for the detection of the sequences containing the label. The detectable labels include any composition capable of generating signals detectable by spectroscopic, photochemical, biochemical, immunochemical, electrical, optical, topological, or chemical means.

The term "detection tag" is a moiety that can be attached to nucleic acid and oligos to produce detection signal intramolecularly or serve as a means for generation of detection signals. A well-known example is biotin as a detection tag and its binding to strepavidin that is modified with a moiety capable of generating detection signals. The detectable tags include any composition detectable by spectroscopic, photochemical, biochemical, immunochemical, electrical, optical, topological, or chemical means.

The term "oligonucleotide" refers to a molecule comprised of two or more deoxyribonucleotides and/or ribonucleotides joining through phosphodiester bonds; the term "oligonucleotide" is not limited to nucleotides of natural types but may include those containing chemical modifications at the moieties of base, sugar, and/or backbone. An oligonucleotide sequence is written in 5'- to 3' direction by convention unless otherwise defined.

The terms "nucleic acid" and "nucleic acid sequence" are used interchangeably to refer to a deoxyribonucleotide or ribonucleotide polymer or oligomer, in either double or single stranded form, and unless otherwise noted would encompass known analogues of naturally occurring nucleotides that can function in the same or similar manner thereto.

The term "primer" refers to a polynucleotide, which is capable of annealing to a complementary template nucleic acid and serving as a point of initiation for template-directed nucleic acid synthesis, such as a polynucleotide amplification reaction. A primer need not reflect the exact sequence of the template but must be sufficiently complementary to hybridize with a template.

The term "duplex" and "double strand" are used interchangeably to refer to at least partial or complete alignment of two strands of oligonucleotides or nucleic acids in an antiparallel orientation with regard to the 5'-terminus of one strand annealed to the 3'-terminus of the other strand.

The term "oligonucleotide mixture" is used to refer to a mixture of at least two or more oligonucleotides which have different sequences.

The term "target sequence" is used to refer to oligos in solution for hybridization with surface probes.

The terms "hybridization" and "binding" in the context of the association of strands of nucleic acid or oligonucleotides are used interchangeably. The term defines reactions which are intended to bring two strands of sequences to form duplexes or at least partial duplexes through base pair formation. Typical hybridization leads to formation of antiparallel duplexes with regard to the 5'-end of each strand. Natural nucleic acid forms base pairs between A and T and between G and T in DNA or G and U in RNA. These are complementary base pairs.

The term "anneal" refers to specific interaction between strands of nucleotides wherein the strands bind to one another substantially based on complementarity between the strands as determined by Watson-Crick base pairing.

The term "stringency" refers to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences and sufficient hybridization stability. Thus, conditions of "weak" or "low" stringency are often required when it is desired that nucleic acids which are not completely complementary to one another or have lower hybridization stability be hybridized or annealed together.

The term "mismatch" refers to lack of complementarity between two nucleotides when aligned. Complementary bases in DNA are A-T and G-C. Complementary bases in RNA are A-U and G-C. Thus a mismatch occurs when two olignucleotide sequences are aligned and at one or more nucleotide positions that an A is not paired with T or a G is not paired with C in DNA or an A is not paired with U or a G is not paired with C in RNA.

The term "perfect match" or "perfectly complementary" refers to a situation in which two oligonucleotides show complete complementarity in a portion of their sequences. Perfect complementarity would exist where two oligonucleotides, one shorter than the other, shared complete complementarity at all nucleotide positions for the length of the shorter oligonucleotide. A shorter oligonucleotide can be "perfectly complementary" even if it is shorter than an oligonucleotide against which it is being matched.

The term "hairpin" refers to a folding and base pair state of an oligonucleotide. A hairpin is formed by intramolecular folding of the sequence to form a base paired duplex region and the two strands of the duplex are connected by a loop structure. A hairpin sequence may be capable of self-templating for the ligation reaction wherein an oligonucleotide can hybridize to the overhang region of the hairpin and oligonucleotide is joined with the short end of the hairpin sequence.

The terms "array" and "microarray" are used interchangeably to refer to a multiplicity of different sites sequences attached to one or more solid supports. The term array can refer to the entire collection of oligonucleotides on the supports (s) or to a subset thereof. The sequences immobilized on the surface in an array through linker and/or spacer are probes or capture probes.

The term "capture probe" refers to an oligonucleotide capable of binding to a target nucleic acid of complementary sequence through one or more types of chemical bonding usually though complementary base-pairing through hydrogen bond formation. The capture probe is designed to be sufficiently complementary to a target oligonucleotide sequence under selected hybridization conditions. As used herein a capture probe may include natural ribonucleotides or deoxyribonucleotides nucleotides such as adenine, guanine, cytosine and thymidine or modified residues, such as those methylated nucleobases, 7-deazaguanosine or inosine, 5'-phosphate, thioate internucleotide linkages, or other modification groups. The nucleotide bases in a capture probe may also be linked by phosphodiester bonds or other bonds (e. g., phosphorothioate) as long as the alternative linkage does not interfere with hybridization. Capture probes may contain or completely are made of locked nucleic acids (LNAs), and/or other modified nucleotide residues, or peptide nucleic acids (PNAs) in which the constituent bases are joined by peptide linkages. The capture probe may contain one or more linkers and/or one or more spacers, and the capture probe may be immobilized through either its 5'- or 3'-end linked to the spacer or linker.

The term "ligated sequence" refers to a sequence which is formed by the ligation of one or more oligonucleotides. The ligation oligonucleotides may include capture probe that has been extended by ligation of one or more oligonucleotides. The term includes ligated oligonucleotides of chain extension whether the ligation performed sequentially or simultaneously by one or more ligator oligonucleotides.

The term "ligation", "ligate", or "ligating" is used in the context that refers the reaction joining two nucleic acid sequences through covalent bonds. Typically, ligation requires a template and hybridization of two sequences with the template strand with the 5'-terminus phosphate group of one hybridizing strand next to the 3'-OH of the other hybridizing strand and formation of a phosphodiester bond by the action of ligase enzymes. Ligation occurs between two duplexes of cohesive ends which are complementary to each other or of blunt ends. Ligation occurs between two single strands which are DNA and/or RNA. The term "ligation" broadly refers to reactions involving gap filling and ligation steps. In the context of the present invention the term "ligation", "ligate", or "ligating" is intended to encompass gap filling which is to add nucleotides to the sequences at the ligation site to make ligatable ends between the two hybridizing sequences aligned with the same template sequence. In the context of the present invention the term "ligation", "ligate", or "ligating" is also intended to encompass other methods of covalently linking such sequences, for example, by chemical means.

The term "ligase" is used to refer to an enzyme used to catalyze ligation reactions. DNA ligase covalently link DNA strands, RNA ligase covalently link RNA strands, some ligase enzymes also catalyze the covalent linkage of RNA to RNA and/or RNA to DNA molecules of single stranded or duplex forms.

The term "ligator" is used to refer to oligonucleotides that can hybridize to form hybridizing duplex containing nicking and/or gapping sites to allow ligation.

The terms "template strand" and "template sequence" are used interchangeably in the context of ligation to refer to the sequence that is at least in part in separate regions, complementary to two sequences. The hybridization of the three strands allows ligation in the form of duplex formation among the three sequences.

The term "self-templation" and "self-templated" are used interchangeably to refer to the fact that the template strand and one of the ligation strands are from the same sequence.

The term "stabilizing agent" is used to refer to reagents or solvents that can stabilize certain structures of nucleic acids, such as duplex or hairpin formation. Examples of such stabilizing agents include polyamines, polymers such as polyethylene glycol, metal ions such as $Co^{2+}$, $Mg^{2+}$, $Ni^{2+}$, $Ni^{3+}$, etc, other types of cationic ions such as poly-lysine, cationic liposomes, polycationic dendrimers, polyethylenimine, $NH^{4+}$, or combination of these reagents.

DETAILED DESCRIPTION OF THE INVENTION

The present invention relates to the simultaneous assembly of two or more elongated oligomers on a solid surface using hybridization and ligation of complementary shorter oligomers. The elongated oligomers produced by the methods of the present invention are addressable since can be located on the solid surface and they are designed sequences in that the sequences synthesized by the methods are not random, but rather deliberately constructed. The present invention relates to the methods of parallel ligation on surfaces using a pool of sequence-specific oligo mixture and various forms of capture probes. The methods of the present invention utilize miniaturization technologies, such as microarray microchips, bead arrays, and single molecule arrays, to be used for (a) simultaneous construction of multiple single-stranded, partially double-stranded and/or doubled- stranded oligos and polynucleotides, including but not limited to DNA, RNA, DNA/RNA hybrids, partial duplexes and duplexes inexpensively and efficiently; (b) more specific and sensitive detection used in genetic analysis; (c) on surface transcription and translation and other biochemical reactions normally run in a test tube as single reactions.

The general scheme of the methods of the present invention can be seen in FIGS. 1-8. FIGS. 1-8 illustrate the methods of the present invention at a single site on surface. These figures are only representative and the methods of the present invention can be used to construct oligonucleotides of known sequence of varying lengths on addressable multiple sites. The methods of the present invention provide for performing these methods on multiple sites sequentially or simultaneously. The oligos used in the methods of the present invention as well as the ligated sequences produced can be the same at each site or may be different at each site. The methods of the present invention even provide for different oligos and elongated oligos to be synthesized at the same site. In the first step of the methods of the present invention a capture probe is placed onto a solid support. The placement of the capture probe on the solid support can be accomplished by "spotting" the pre-synthesized capture probes onto the support; alternatively capture probes can be placed onto the solid support by de novo synthesis of the capture probe on the solid support (Gao, Zhou, and Gulari 2004). The methods of the present invention are not limited by the method of attachment of the capture probe to the surface, nor are the methods of the present invention limited by the type of surface utilized. There are many known methods of making DNA and RNA chips that can be utilized in the methods of the present invention. The capture probe may also be attached to the solid support through immobilization of linkers and/or spacers which are well known by those skilled in the art. The orientation of the capture probes may be in the direction of either the 3'→5' or 5'→3', and in the case where the capture probe is synthesized de novo, the appropriate selection of linkers and/or spacers and/or nucleotides to achieve the desired orientation is required. When capture probes are linked to ligators through their 5'-end group, the 5'-OH should be converted to 5'-OPO$_3$ by chemical or biochemical phosphorylation or restriction nuclease enzymatic cleavage.

In a preferred embodiment of the present invention, shown in FIG. 1, the capture probes are secured to the solid support, and then target nucleic acid sequences of single-stranded or duplex are added to the capture probes and hybridized to the capture probes under specific hybridization conditions. In some or all cases, upon hybridization, a portion of the target sequences forms a duplex with the capture probes but a region of the target sequences is single-stranded. After the hybridization of the target sequences and capture probes, ligation oligos (ligators) that are specific to the portion of the target sequences which is adjacent to the capture probe sequence are added and hybridized to the single-stranded region of the target sequences in the capture probe-target sequence duplexes. The design of the capture probe and ligator oligo provides that after the above steps are completed that both sequences are hybridized to the same target sequence and one end of the capture oligo and one end of the ligator are in close proximity such that ligation of the capture probe and ligator oligo can be effectuated by the addition of ligase under appropriate conditions. The ligation of capture probe and ligator oligo extends the chain length of the original sequences and the resultant product is called a ligated nucleic acid sequence.

Figure 2:
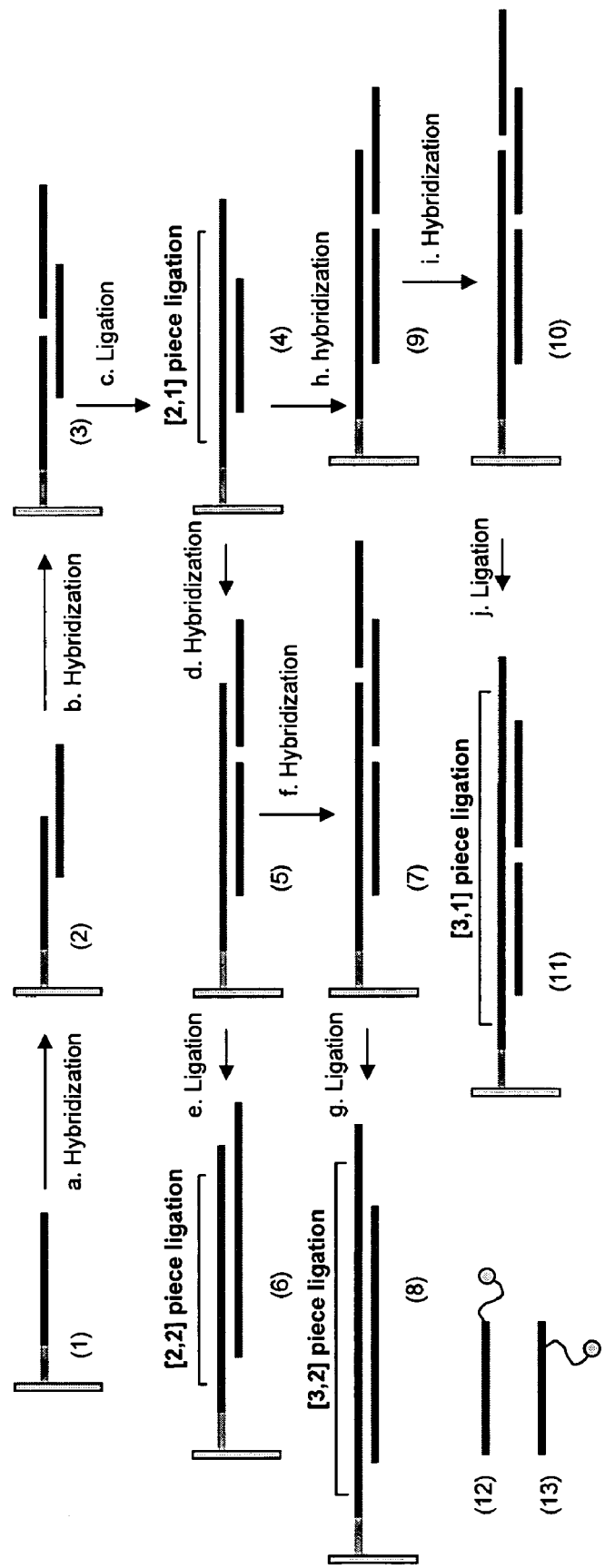
FIG. 2—Schematics of the hybridization-ligation procedures for making single strand or duplex nucleic acids. (a) A plurality of oligos on surface and a first oligo mixture containing sequences, which partially complement to the sequences of hybridization, are applied to the surface. (b) A second oligo mixture containing sequences that partially complement to the sequences of hybridization are applied to the surface. (c) Performing ligation reaction to extend the length of the sequences on surface. (d) A third oligo mixture containing sequences that partially complement to the sequences of hybridization are applied to the surface. (e) Performing ligation reaction to extend the lengths of both strands of the duplexes. (f) A fourth oligo mixture containing sequences that partially complement to the sequences of hybridization are applied to the surface. (g) Performing ligation reaction to extend the length of both strands of the duplexes. (h) Alternatively, a third oligo mixture containing sequences that partially complement to the sequences of hybridization are applied to the surface. The oligos hybridized do not allow ligation with the adjacent strands. (i) A fourth oligo mixture containing sequences that partially complement to the sequences of hybridization are applied to the surface. (l) Perform ligation reaction to extend the length of the sequences on surface. Species #12 and #13 contain labels for detection. Examples labels may be fluorescent molecules, affinity tags for conjugation antibody, conjugated avidin/streptavidin, nucleic acid sequences, or other molecules that directly or indirectly provide detection signals.

As can be seen in FIG. 2 the steps of adding another target/ligator as an oligo mixture, hybridization of these oligos to the capture probes in the initial cycle and to the single-stranded region of the surface sequences in repetition cycles can be repeated multiple times. Ligation with the hybridizing duplex provides a single-stranded, double-stranded, or partially double-stranded oligos of known length and sequence. The oligonucleotides may contain labels for detection. There are many molecules that may serve as labels for examples labels may be fluorescent molecules, affinity tags for conjugation antibody, conjugated avidin/streptavidin, nucleic acid sequences, or other molecules that directly or indirectly provide detection signals. The methods of the present invention contemplate that the hybridization and ligation steps after the initial hybridization to the capture probe can be performed in combination and/or at different orders throughout the process. The addition of the oligo mixture may be serial (sequential), simultaneous, or a combination thereof. For example, after the initial hybridization of the oligo mixture to the capture probe, the stepwise addition of oligo mixture for hybridization and ligation steps (FIG. 2, steps b, c, d, e) result in nucleic acid polymer of extended chain length. Representative examples of the ligated sequences are shown in FIG. 2 (species 4 and 6). Alternatively, the stepwise addition of oligo mixture for hybridization may be repeated more than once, and the ligation step is then performed (FIG. 2, steps d, f, and g, or steps h, i, and j). These reactions result in nucleic acid polymer of extended chain length. Representative examples of the ligated sequences are shown in FIG. 2 (species 8 and 11). Also alternatively, the steps of addition of oligo mixture for hybridization and ligation can be performed in combination and the reaction result in nucleic acid polymer of extended chain length, and the representative examples of the ligated sequences are shown in FIG. 2 (species 4, 6, 8 and 11). The steps of addition of oligo mixture for hybridization and ligation shown in FIG. 2 can be performed as described for assembly of nucleic acid polymers of desired chain length. Under circumstances where an application may require single strand products, one of the strands may be formed from oligos of non-ligatable 5'- or 3'-ends, and thus ligation will only join one of the two strands. Alternatively, after the ligation reaction at various steps the sequence hybridizing to the ligated sequence can be melted away to leave the ligated sequence as single-stranded. The chain length extension is continued by adding and hybridizing oligo mixture to the ligated sequence and providing a duplex region at the end of the ligated sequence continuing with a single strand region which can hybridize with a second oligo mixture. The reactions are repeated in the manner similar to what discussed above for FIG. 2 species 4, 6, 8, and 11, resulting in formation of at least partially single-stranded nucleic acid polymer. Therefore, the methods of the present invention include combination of sequential and simultaneous addition, hybridization, and ligation. The choice of whether to employ sequential, simultaneous or a combination of approaches is determined by various factors for optimization including but not limited to the length of sequences to be produced, total number of sequences produced, and type of ligation enzyme employed.

In the present invention, the formation of duplex and elongation nucleic acid sequences may include those of nucleotide analogs for the purposes of alter the properties, such as stability or adding labeling tags, of the nucleic acid synthesized. The nucleotide analogs, such as locked nucleic acid (LNA) and thioate nucleic acids, are known to be substrate of DAN synthesis enzymes, have been shown to form duplexes which are more stable or more resistant to enzymatic degradation, respectively.

In the present invention, the formation of duplex and elongation nucleic acid sequences may be facilitated by stabilizing reagents and/or conditions (Sarkar et al. 2005). Examples of stabilizing agents include polyamines, polymers such as polyethylene glycol, metal ions such as $Co^{2+}$, $Mg^{2+}$, $Ni^{2+}$, $Ni^{3+}$, etc, other types of cationic ions such as poly-lysine, cationic liposomes, polycationic dendrimers, polyethylenimine, $NH^{4+}$, or combination of these reagents. The presence of these compounds is known to increase the affinity of the strands of nucleic acids. In particular for nucleic acid synthesis, the presence of stabilizing reagent should not interfere with the necessary enzymatic reactions such as ligation and PCR. In this regard, solid surface synthesis or assembling of nucleic acid sequences allows the use of stabilizing reagent even though it is incompatible with the necessary enzymatic reactions such as ligation and PCR. This is because the undesirable stabilizing reagent can ben replaced with wash solution and suitable reaction solution.

The illustrations of the present invention shown in FIGS. 1 and 2 involve the use of an oligo mixture of defined sequences, which may serve as hybridizing sequences that are template for ligation reaction and/or as ligators that can be ligated to capture oligos or hybridizing or ligated sequences to produce longer, ligated sequences. The oligos in an oligo mixture can be made by conventional synthesis methods which produce one sequence at a time followed by mixing of all the single sequences synthesized. In a preferred embodiment of the present invention the oligo mixture utilized is produced in an array synthesis device that produces many oligos of varying sequences and these are cleaved from the surface to directly produce a pool of oligo mixture. This oligo mixture can be used directly in the methods of the present invention or alternatively these oligos may be enzymatically amplified. The oligos have the proper terminal groups (5'-P and/or 3'-OH terminal groups) necessary for ligation. The methods of the present invention include preparation of mixtures of oligos by synthesis on support materials such as controlled porous glass (CPG) or polymers such as polyethyleneglycol, polystyrene, polypropylene, or co-polymers of these. Support materials may also include composite materials, such as a support film on a solid substrate. The support film may be made of materials including but not limited to CPG, sol gel, polyethyleneglycol, polystyrene, polypropylene, or co-polymers of these. The solid substrate may include but not limited to glass, silicon, ceramics, plastics, and metals. The solid substrate may be shaped as a slab, a wafer, a sphere, a plate containing various features such as wells, trenches, basins, and holes for fluid transportation, confinement, and any other appropriate functions. Obviously, variations and combinations of the above mentioned materials can be used as supports for the synthesis of oligos or oligo mixtures of the present invention. Oligo mixtures may also be prepared by parallel synthesis on an array which use photolabile protecting groups, photogenerated acids and 4,4'-dimethoxytrityl (DMT) nucleophosphoramidites (phosphoramidites), electrochemically generated acids and DMT phosphoramidites, or inkjet printing DMT phosphoramidites (Gao, Gulari, and Zhou 2004).

A useful property of the ligated sequences is the presence of priming sites (FIG. 1C1, 1C2; FIG. 3, species 6b; FIG. 4A, species 5), which may be specific sequences or common in several or all ligated sequences. Examples of these priming regions include promoter sequence for transcription and universal primers for PCR. Therefore, the ligated sequences can be templates for RNA synthesis or they can be amplified for various applications, such as more sensitive detection of the ligated sequences and as a method of creating DNA libraries. The incorporation of different priming regions for different oligos synthesized which are used for making ligated sequences may be sued to generate subsets of oligo mixtures from one array synthesis. After hybridizing and ligation reactions, PCR reactions may be performed separately using the corresponding complementary primers using the oligo mixture. This results in amplification in each PCR reaction a specific subset of the oligo mixture. Alternatively the subsets of oligomixture may be generated by labeling these with different tags, such as specific nucleic acid sequences that can be separated by selective hybridization of their complementary sequences or biotin and amino terminus which can be separated by their different affinity binding targets.

The oligo mixtures used in the methods of the present invention may be purified to remove part or all impure oligos. Impure oligos are those which contain one or more substitution(s), and/or insertion(s) and/or deletion(s) of nucleotides when compared to the desired designed sequences. Impure oligos also include truncated forms of desired oligos (i. e., those of less than full length). Oligos may be purified by chromatographic methods, such as reverse phase or ion-exchange columns, or by gel electrophoresis. Purification may also be achieved by hybridization of the oligos to another mixture of oligos of complementary strands immobilized on surface (Tian et al. 2004, Zhou et al. 2004). The degree of purity can be controlled by the hybridization conditions used for improving the specificity of hybridization. The impure oligos form less stable duplexes and these sequences are washed off the surface while the stable duplex formation retains those of the desired oligos. The desired oligos are then recovered by stripping the hybridized sequences using an aqueous solution. In the present invention, the hybridization step in preparation for ligation can be optimized to achieve oligo purification. Purification of oligo mixtures can be achieved enzymatically (Smith and Modrich, 1997) and/or by ligand interactions (Gao and Han, 2001) in which ligands selectively recognize unusual structures of oligo duplexes such as mismatch base pair, bulge, loop, nick, or depurination sites. These reagents can be used to assist the removal of impure oligos and impure ligated sequences due to the incorporation of impure oligos.

The present invention provides methods for reducing the errors in hybridized and/or ligated sequences. In one preferred embodiment of the present invention, nucleic acid binding proteins, such as MutS and/or MutL which discriminately bind to mismatch base pairs and aberrant nucleic acid structures, are applied to hybridized and/or ligated sequences on surface. The protein bound DNA sequences can be separated from free DNA sequences using methods well-known by those skilled in the art. The releasing of the hybrizing and/or ligated sequences from surface can be performed before or after the protein binding. The separation removes error-containing sequences from the correct sequences and thus achieves higher quality for the hybridizing and/or ligated sequences.

The methods of the present invention include the synthesis of polymers of nucleic acids in either the 3'→5' or 5'→3' direction. Therefore, in the methods of the present invention capture probes may be anchored to the solid support in such a way that the end that is away from the surface of the attached capture probe is either 5' or 3'. In an embodiment of the present invention, the capture probe may have one terminus of the sequence as either 5'-phosphate or 3'-OH oriented away from the surface. The 5'-phosphate in the capture sequence may be ligated with 3'-OH of the adjacent ligator oligo or the 3'-OH in the capture sequence many be ligated with 5'-phosphate of the adjacent ligator oligo.

Figure 5:
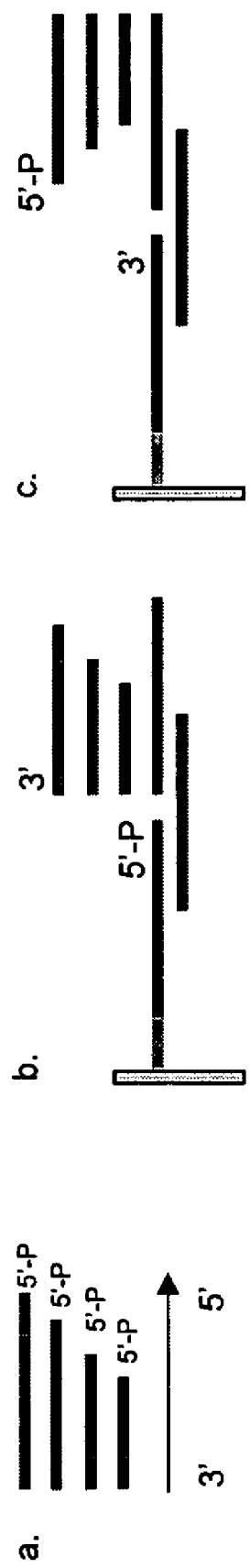
FIG. 5—Comparison of the ligation reactions using initiated by oligos of different orientation with regard to the 5'-end of the sequences. (a) Illustration of the synthesis of ligation oligos. Normal synthesis is in the direction of 3' to 5', which produces full length sequences; the associated failure sequences mostly would have the correct 3'-end but short in length and more errors towards the 5'-end. (b) Initiation of ligation by linking the surface strand with 5'-phosphate and the ligation oligos with 3'-OH. The failure sequences would hybridize to form ligation sites, but such ligation results in sequences less than the desirable lengths and further terminating the subsequent ligation reactions. (c) initiation of ligation by linking the surface strand with 3'-OH and the ligation oligos with 5'-phosphate. The failure sequences would not form the correction ligation site and are washed off after the ligation reaction. The purity of ligation reaction is improved.

The present invention provides method for improving the quality of ligated sequences by initiation of ligation as shown in FIG. 5. As previously stated the methods of the present invention permit the synthesis of oligos and their subsequent longer sequences to proceed in either a 5'→3' or 3'→5' direction. This produces capture sequences having either 3'-OH or 5'-phosphate end, respectively, away from the surface (FIG. 1A1 and 1A2; FIG. 5, b and c). Traditionally, oligos have been synthesized in a 3'→5' direction and such synthesis normally produces failure sequences having the desired 3'-end but may be truncated or have substitution, deletion or other errors nearer the 5'-end. Therefore, if the capture probe synthesized by traditional method has free 5'-phosphate, its ligation with ligator requires the 3-'OH end of the ligator sequences. This form of ligation results in incorporation of many failure ligator oligos which have the correct 3'-end but may be truncated or have deletion or substitution or other errors nearer the 5'-end. Alternatively, if the capture probe synthesized in 5'→3' direction has free 3'-OH, its ligation with ligator requires the 5'-phosphate end of the ligator sequences. This form of ligation results in incorporation of mostly fill-length sequences, and thus higher quality of ligated sequences. Therefore, in a preferred embodiment of the present invention the capture probe and ligator oligo mixture are synthesized in opposite orientations. In a more preferred method of the present invention the capture probe is synthesized in a 5'→3' direction and the ligator oligo mixture is synthesized in a 3'→5' direction.

The methods of the present invention may use oligo mixture labeled with one or more detection tags (FIG. 2. species 12 and 13). Examples of detection tags include fluorescent molecules, chemiluminescence molecules, nanoparticles of useful optical properties such as emission, resonance energy transfer, anisotropy, and quenching. Useful labels in the methods of the present invention include biotin for staining with labeled streptavidin conjugate, magnetic beads, fluorescent dyes, radiolabels (e.g. $^3$H, $^{125}$I, $^{35}$S, $^{14}$C and $^{32}$P), enzymes (e.g. horse radish peroxidase, alkaline phosphatase, and other commonly used in ELISA) and colorometirc labels such as colloidal gold (e.g. gold particles in the 40-80 nm diameter range scatter green light with high efficiency) or colored glass or plastic (e.g. polystyrene, polypropylene, latex, etc.) beads, and those which mediate the attachment of detection signaling molecules such as biotin, nucleic acid oligomer, peptide sequence, dendrimer, and gold particle. Preferred labels are fluorescent moieties including but not limited to those based on fluorescein, rhodamin, cynine, and other photogenic moieties available commercially (Molecular Probe/Invitrogen, CA, USA). Attachment of the detection tags to the oligos can be by direct attachment (e.g. covalent) with or without a linker moiety, or by non-covalent binding such as hybridization. The attachment position of the detection tag to the oligo may vary depending on the type of detection tag and different ligation scheme requirements. For example, a label may be attached to a nucleoside, nucleotide or analogue thereof at any position that does not interfere with hybridization, detection or ligation. The choice of detection tag and the positioning of the tag on the oligo should be such that the oligo can hybridize to and be ligated with other nucleic acid sequences as illustrated in the present invention. In some cases, the labeled detection tag is removed or silenced before the incorporation of another detection tag by the subsequent hybridization and/or ligation. The methods of the signal removal differ depending on the tag molecules used. For fluorescent molecules, photobleaching is possible. Incorporation of a cleavable linkage at the attachment site is an alternative method. Hybridization and/or ligation can then be monitored at each step. The signals from hybridization can be removed by stripping the hybridizing sequences, but under such conditions, the signals from ligation remain due to covalent bond formation (FIG. C1 versus E1, C2 versus E2; FIG. 10C versus 10F). The monitoring of the hybridization and ligation reactions may help optimizing the efficiency of these reactions.

The present invention provides methods for detection of hybridizing and/or ligated sequences through parallel ligation reactions using sequence-specific ligation oligos containing detection tags. The methods provide increased specificity due to the selection of perfect match duplexes by hybridization and ligation. Modified oligos such as those containing locked nucleic acid (LNA) residues may enhance the $T_m$ and specificity of duplexes (Vester and Wengel, 2004). The suitable choices of modifications for incorporation into the capture probes and/or ligator sequences further improve the specificity of hybridization and ligation for high fidelity synthesis of long nucleic acid sequences.

The single-stranded, double-stranded and partially double-stranded ligated sequences of nucleic acids generated by the methods of the present invention can be used in a variety of applications well-known to those skilled in the art of nucleic acid technologies. The ligated sequences made by the methods of the present invention may be used while attached to the solid support or the ligated sequences may be used after they have been removed from the solid support. Removal of the ligated sequences can be effected by chemical or enzymatic cleavage. The use of chemical or enzymatic cleavage will depend on the type of linker or spacer used to attached the capture probe to the solid support. Selected choices of the linkages that can be used to release the attached sequences from surface are described in US Patent Application 20030120035, incorporated herein by reference in its entirety.

One example of an application for the ligated nucleic acid sequences made by the methods of the present invention is amplification of the ligation products using methods well-known to those skilled in the art, such as PCR, rolling circle amplification (RCA), or isothermal amplification. The presence of a priming sequence in the ligated sequences allows amplification reaction either on solid surface or in solution after releasing of the ligated sequences from surface. Amplification is an effective way to improve sensitivity in detection of ligation products by incorporation of detection tag during the amplification processes or thereafter. Alternatively, the ligated sequences may contain a specific tag, such as specific oligo sequence, which can hybridize with amplified detection signals such as dendrimer that contains the complementary strand and thus hybridize to the specific oligo in the ligated sequence, or biotin which binds tightly to avidin or streptavidin labeled with detection molecules. It is common to use multi-layers of binding complex, such as biotin-streptavidin to achieve signal amplification.

The DNA sequences synthesized as described have broad applications well-known to those skilled in the art of DNA technologies. One of the advantages of the prescribed method is to produce artificial DNA sequences of any sequence design and any lengths. Such DNA fragments are useful as synthetic genes or materials for large DNA assembling (Zhou et al. 2004; Tian et al. 2004). The DNA sequences may be made to well-defined lengths and sequences as molecular size markers for characterization of biological DNA fragments.

The DNA sequences synthesized as described have broad applications well-known to those skilled in the art of RNA and protein technologies. In one preferred embodiment, the ligated DNA sequences contain a transcription initiation site, such as a T7 promotor sequence. The ligated DNA sequences may be attached to surface or in solution and serve as template strands for transcription of RNA sequences in parallel or in a multiplexing form, respectively. The parallel transcription reactions produce an array of RNA sequences, which has applications for probing interactions with RNA molecules and for on-surface protein expression using commercial kits (Roche and Promega) of cell-free protein expression. There are various methods used for immobilizing proteins/peptides after their expression, such as ribosome display (Hanes and Pluckthun (1997)), RecA attachment (Odegrip et al. (2004)), and puromycin mRNA display (Roberts and Szostak (1997)). The immobilization of proteins and peptides produced by the large number of ligated DNA sequences provides an effective means for generation of microarrays of proteins or peptides of defined sequences.

An array of nucleic acids or protein/peptides made by the methods of the presence invention has applications for creating and studying cell microarrays. The specific interactions of the synthesized nucleic acids or protein/peptides with cell surface receptors cause immobilization of cell, and the subsequent infusion of these molecules on surface into the immobilized cells provide opportunities for applications of cell content screening and in vivo studies. The methods of the present invention can be used to construct antibody libraries which can be used for multiplex mutagenesis studies.

Figure 3A:
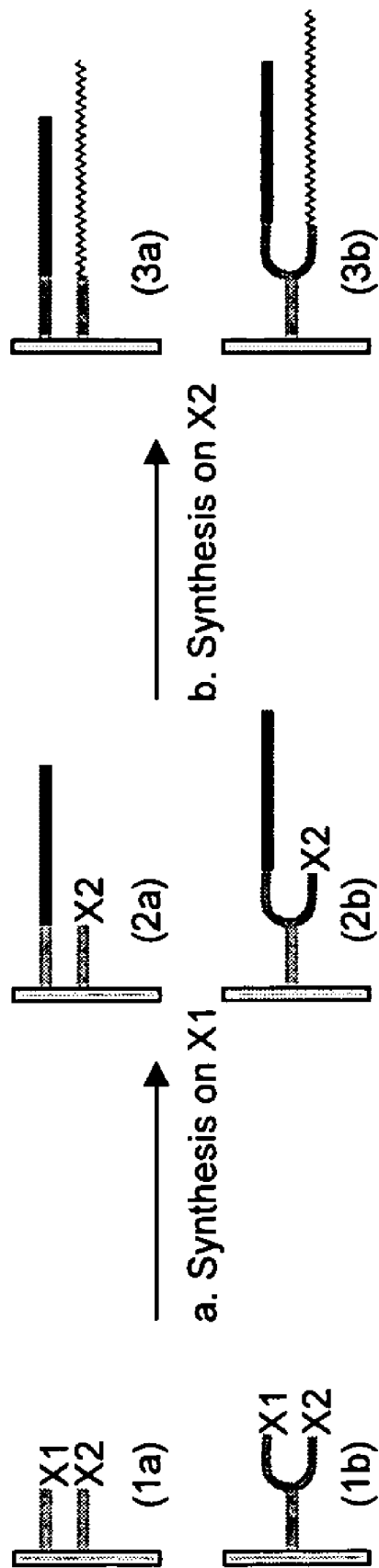
FIG. 3A—Illustration of preparation of surface probe oligonucleotides using orthogonal synthesis. X1 and X2 are distinctly different chemical moieties and are protecting groups. Removal of X1 and/or X2 will expose functional groups, such as OH or NH2 to allow coupling with the incoming building blocks such as nucleophosphoramidites. X1 and X2 may be removed by distinctly different reaction conditions. For instance, X1 may be a DMT group which is removed under acidic conditions and X2 is the Fmoc group which is removed under basic conditions. After the removal of the first protecting group, the synthesis of oligos is carried out using the well-known methods for making sequences on solid support. The X2 group is subsequently removed, and the synthesis of oligos is carried out using the well-known methods for making sequences on solid support. The surface may contain a plurality of protecting groups which can be differentially deprotected to allow the synthesis of a plurality of oligonucleotides of different sequences.
Figure 3B:
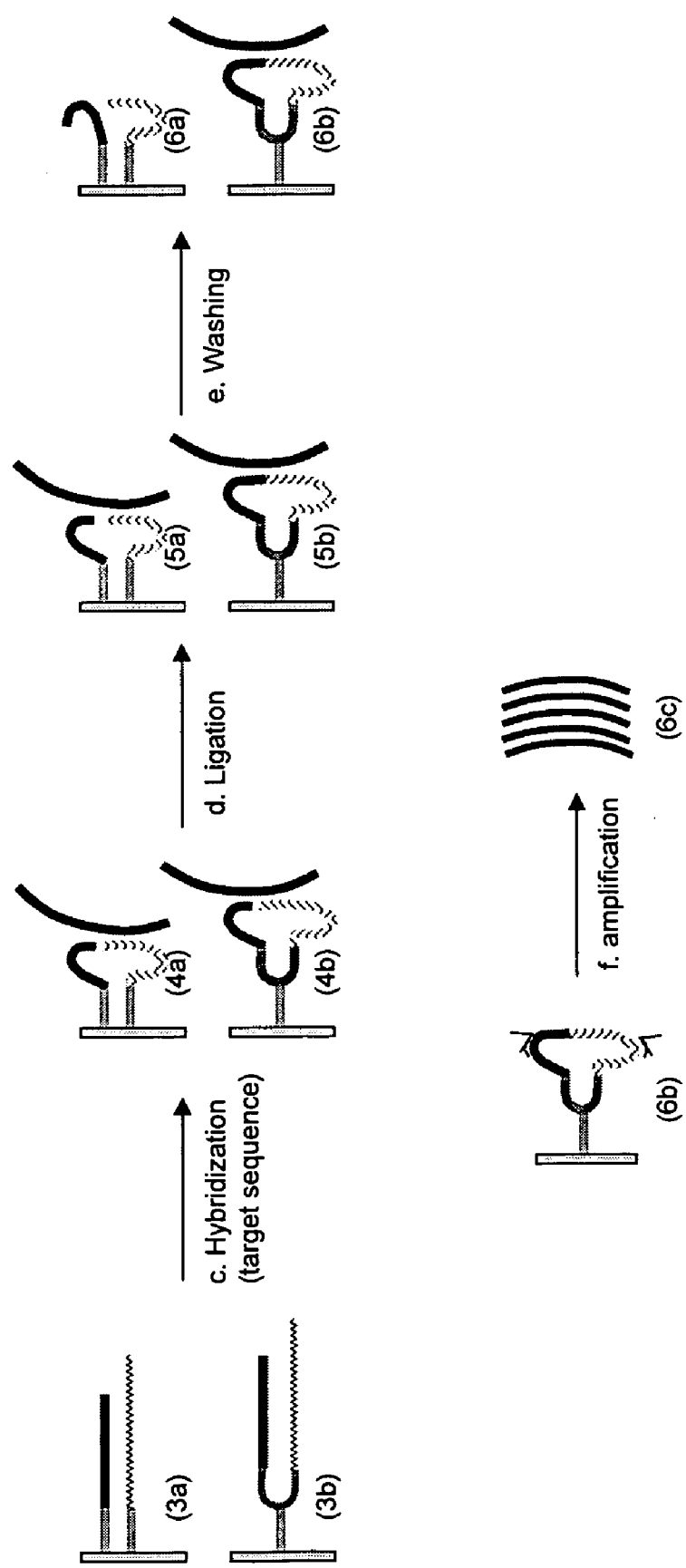
FIG. 3B—Illustration of the ligation on chip using orthogonal synthesis. (c) The two kinds of strands within the same reaction site are in an antiparallel orientation and form a capture probe. A sample of target sequence is hybridized with the probe strands. (d) Ligation reaction is performed on surface. (e) Under stringent wash-stripping conditions the target sequences hybridized to the ligated capture probes are retained on surface, but those partially hybridized to the incorrect capture probes are removed from surface. (f) The ligated loop on surface is used as template for amplification, such as PCR or isothermal amplification. In one preferred embodiment of the present invention, at least one primer is labeled with detection signal, such as fluorescent dye or chemiluminescence-generation moiety as those widely used in biochemical and biological assays of nucleic acids or proteins.
Figure 4A:
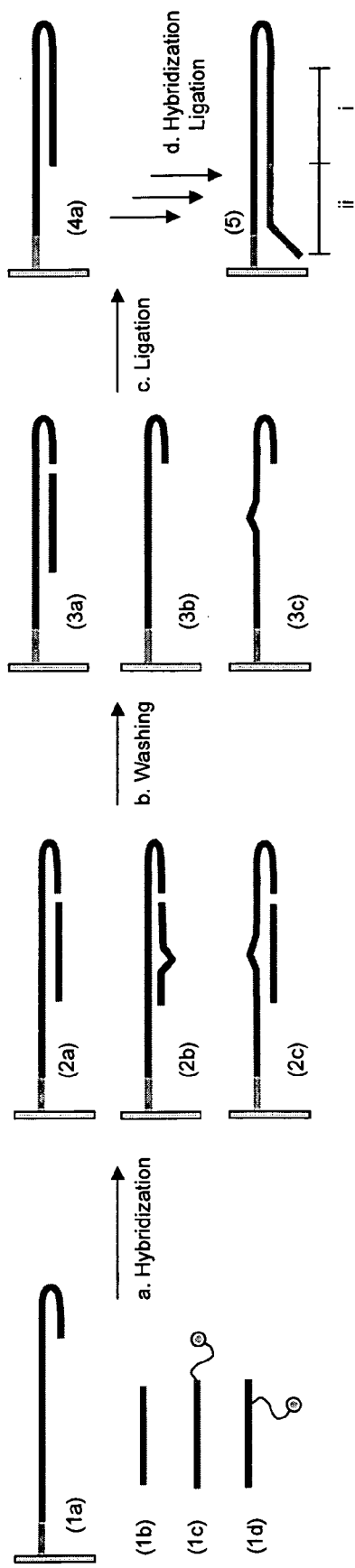
FIG. 4A—A schematic illustration of target hybridization and ligation using self-templating hairpin sequence for detection of nucleic acid sequences according to their sequence and in certain cases their length. The procedure is also useful for detection based on specific sequences. (a) A plurality of oligos on surface which are self-templated sequences (1a) and a first mixture of oligos (1b, 1c, and/or 1d) or target sequences are applied to the surface. (b) More stringent hybridization conditions such as low concentration buffer or a solution which promotes dissociation of hybridized sequences are applied to the surface. Hybridization results in formation of complementary duplexes (2a) and those containing mismatch or misaligned sequences (2b and 2c). The washing step leaves complementary duplexes on surface. (c) Ligation produces a single strand hairpin sequence. (d) multiple steps of hybridization and ligation. Example product (5) is derived from ligation of fragments ii and i.

The present invention provides methods for using a plurality of probes on surface for hybridization and ligation with target sequences as shown in FIGS. 3A and 3B. FIG. 3A illustrates preparation of surface probe oligos using orthogonal synthesis where a functionalized surface contains a plurality of different protected functional groups within the same reaction site on surface, such as X1 and X2, and where X1 and X2 are distinctly different chemical moieties and are protecting groups. Removal of X1 and/or X2 will expose functional groups, such as OH or $NH_2$ to allow coupling with the incoming building blocks such as nucleophosphoramidites. X1 and X2 may be removed by distinctly different reaction conditions. For instance, X1 may be a DMT group that can be removed under acidic conditions while X2 is the Fmoc group that can be removed under basic conditions. In a preferred embodiment, the orthogonal protections are from asymmetric doubler (Glen Research, Sterling, Va. USA) or from surface bound N-α-Fmoc-N-ε-tBoc-L-lysine (LC Sciences, Houston, Tex. USA). After the removal of the first protecting group, the synthesis of oligos is carried out using methods for making oligo sequences on solid supports. The X2 group is stable during the synthesis of oligos extending of the sites which originally were protected by X1 and subsequently removed. The synthesis of oligos is then carried out using methods for making sequences on solid support. The synthesis results in two different oligos made within the same reaction site.

The surface may contain a plurality of protecting groups that can be differentially deprotected to allow the synthesis of multiple oligos of different sequences. The surface linker or spacer molecules are not limited to only two branches but multiple branches such as those found in dendrimer molecules. Useful dendrimer molecules include trebler phosphoramidites. (Glen Research, Sterling, Va. USA).

The present invention provides method for using a plurality of oligo probes in the same reaction location using orthogonal synthesis on surface for hybridization and ligation with target sequences comprising the steps shown in FIG. 3B where a plurality of oligos are paired on a surface (3a and 3b). The pair of sequences is oriented in an antiparallel fashion where the two terminal sequences furthest from the surface are designed so as to join to form a capture probe for a specific target sequence. The capture probe hybridizes with target sequence to form duplexes of both probes as the complementary strands of the target sequence. Thereafter ligation is performed followed by washing to produce duplex sequences from those that are correctly hybridization and ligated. The detection of the target sequence on surface may be obtained by labeled signal on the target sequence. In one preferred embodiment of the present invention, the labeled signal is a fluorescent dye moiety, emitting signal at wavelengths in the range of 480-700 nm. In another preferred embodiment of the present invention, the labeled signal is a from a chemiluminescence generator, such as the horseradish peroxidase system.

The different sequences in the same reaction location may form a loop structure by hybridization with a target sequence and ligation as shown in FIG. 3B. The ligated loop on the surface can be used as template for amplification, such as PCR or isothermal amplification. In one preferred embodiment of the present invention, at least one primer is labeled with detection signal, such as fluorescent dye or chemiluminescence-generation moiety as those widely used in biochemical and biological assays of nucleic acids or proteins.

Figure 3C:
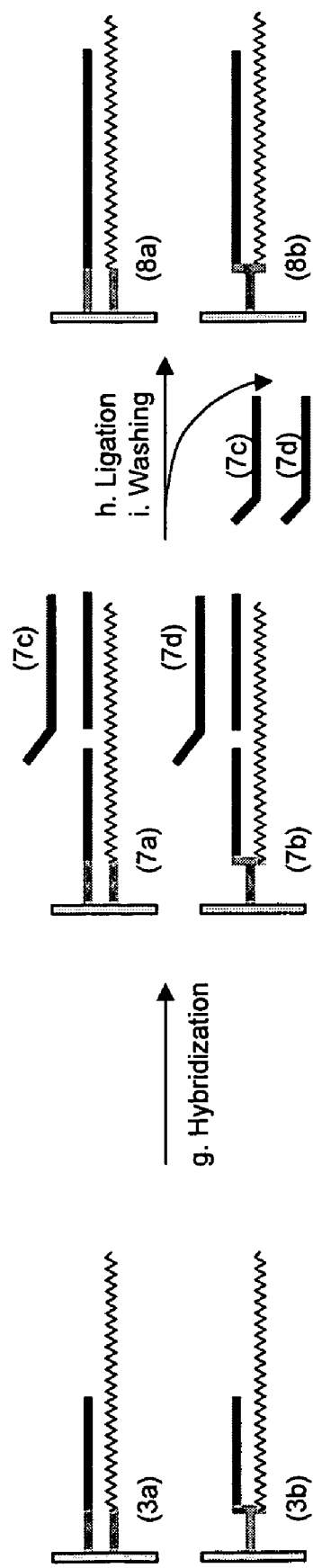

The pairing of probes at the same reaction location can also be used in the fashion described in FIG. 3C where the pair of sequences is oriented in an antiparallel fashion with respect to the 5'-terminus and is at least partially a duplex. Target sequences of various lengths are hybridized to the surface probes (FIG. 3C, 7a and 7b as hybridized duplexes or 7c and 7d as alternative hybridizing strands). The pair of the probe sequences is synthesized with the surface functionalized with orthogonally protected groups. Typically, one surface group is blocked by at least one acid labile protecting group and the other is blocked by at least one base labile protecting group. After synthesis, one of the sequences in the pair is longer and the single strand region is specific for a target sequence by hybridization. Ligation followed by washing produces a ligated duplex sequences from the sequences that have the correct ligation alignment and target sequences of the correct terminus sequence (FIG. 3C, 8a and 8b).

The present invention describes the use hybridization and ligation procedures applied to a self-templated sequence. The steps of hybridization and ligation may be multiple and are not limited to what described in FIG. 4A. An application of using self-templated capture probes provides method of producing ligation products as single stranded hairpins (FIG. 4, species 4a and 5). The stringent wash steps used in combination with ligation help the removal of erroneous sequence and thus improve the quality of the ligated sequence. An application of the hairpin oligos is to use in expression of small interference RNA (siRNA) oligos using plasmid vectors. A large number of hairpin oligos are synthesized, cloned into a vector for in vivo or in vitro expression (Paddison et al. 2004). The hairpin oligos of improved quality produce more correct vectors than those produced by direct synthesis of the full length hairpin sequences.

The present invention provides methods for the detection of sample sequences based on specific sequences and lengths by using a combination of hybridization and ligation reactions in multiple steps (FIG. 4A). In one preferred embodiment, the first ligation sequences are sample molecules and are hybridized and ligated to self-templated probes (FIG. 4A, species 3a and 4a). In one preferred embodiment of the present invention, the target molecules are small RNA molecules, especially these are miRNA molecules from total biological RNA. The second hybridizing sequences in an oligo mixture specifically complement to the template strand at the region that is immediately adjacent to the first ligation region. In the presence of specifically designed self-templated probes, the ligation product formation from both ligation steps correctly identifies the sequences and the lengths of the first ligated (sample molecules) sequences (FIG. 4A, species 5).

Figure 4B:
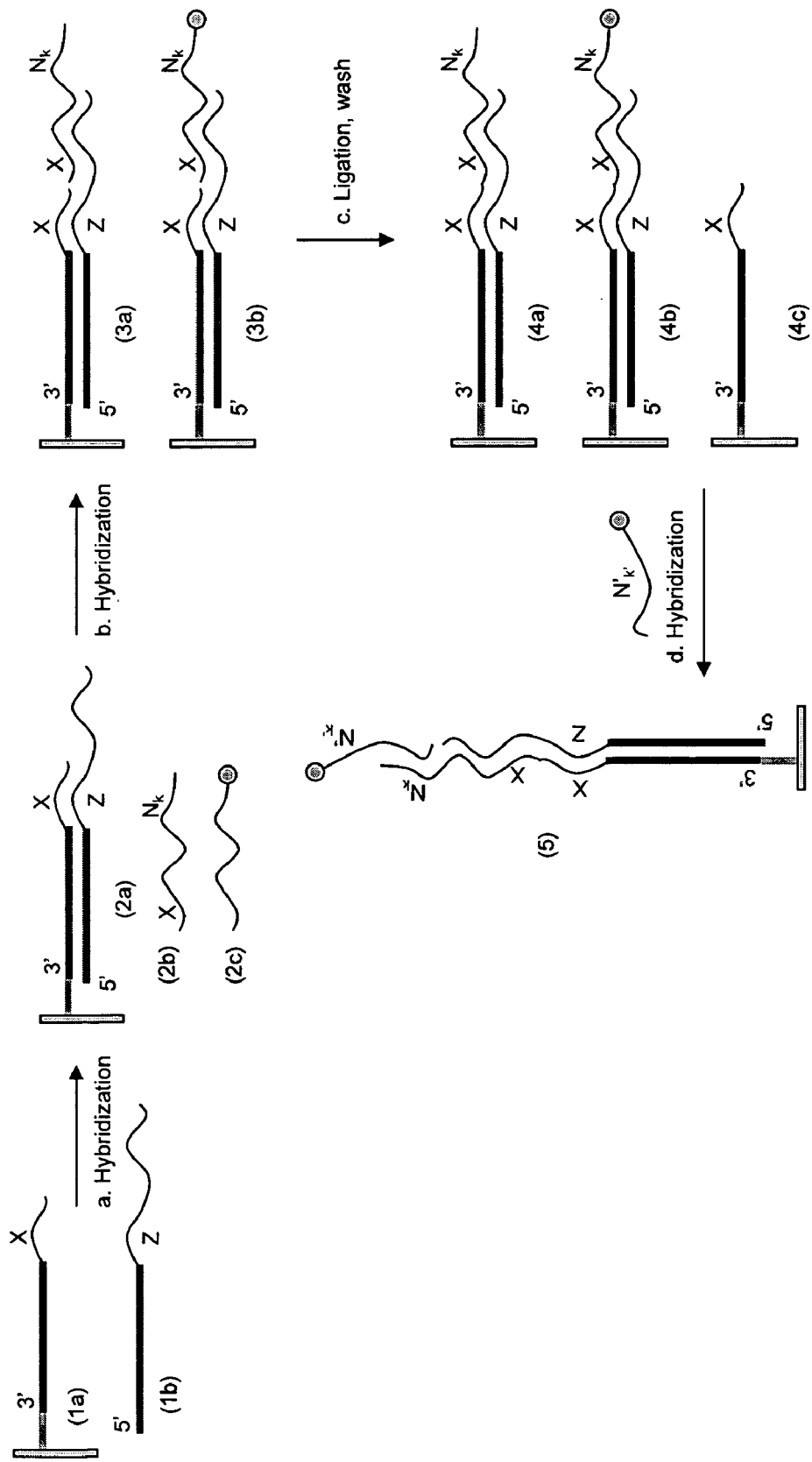

In a preferred embodiment of the present invention as shown in FIG. 4B, the capture probe contains a variable region (shown as straight lines) which is specific to the target sequence (FIG. 4B, species 1a and 1b, respectively) and an extension of T oligomer which may incorporate LNA or other modified nucleotides that can alter $T_m$ of the hybridizing duplexes, and the incorporation of these non-natural nucleotides is immediate to the variable region. The first hybridization of the sample target sequence to the capture probe provides an overhang in the sample target strand; the second hybridizing oligo with or without labeled with a detection tag is then partially hybridized to the overhang and may also extend to provide a second overhand in the capture probe strand (FIG. 4B, species 4a and 4b). Such hybridization and ligation can be repeated for bringing suitable detection tag and to introduce more detection tags into the ligated sequences, facilitating the detection of sample target sequences. One preferred embodiment of the method shown in FIG. 4B is the detection of miRNA, which are small RNA target sequences of less than 25-mer long. The introduction of the detection tag by hybridization and ligation increases sensitivity and specificity of miRNA detection.

Figure 10:
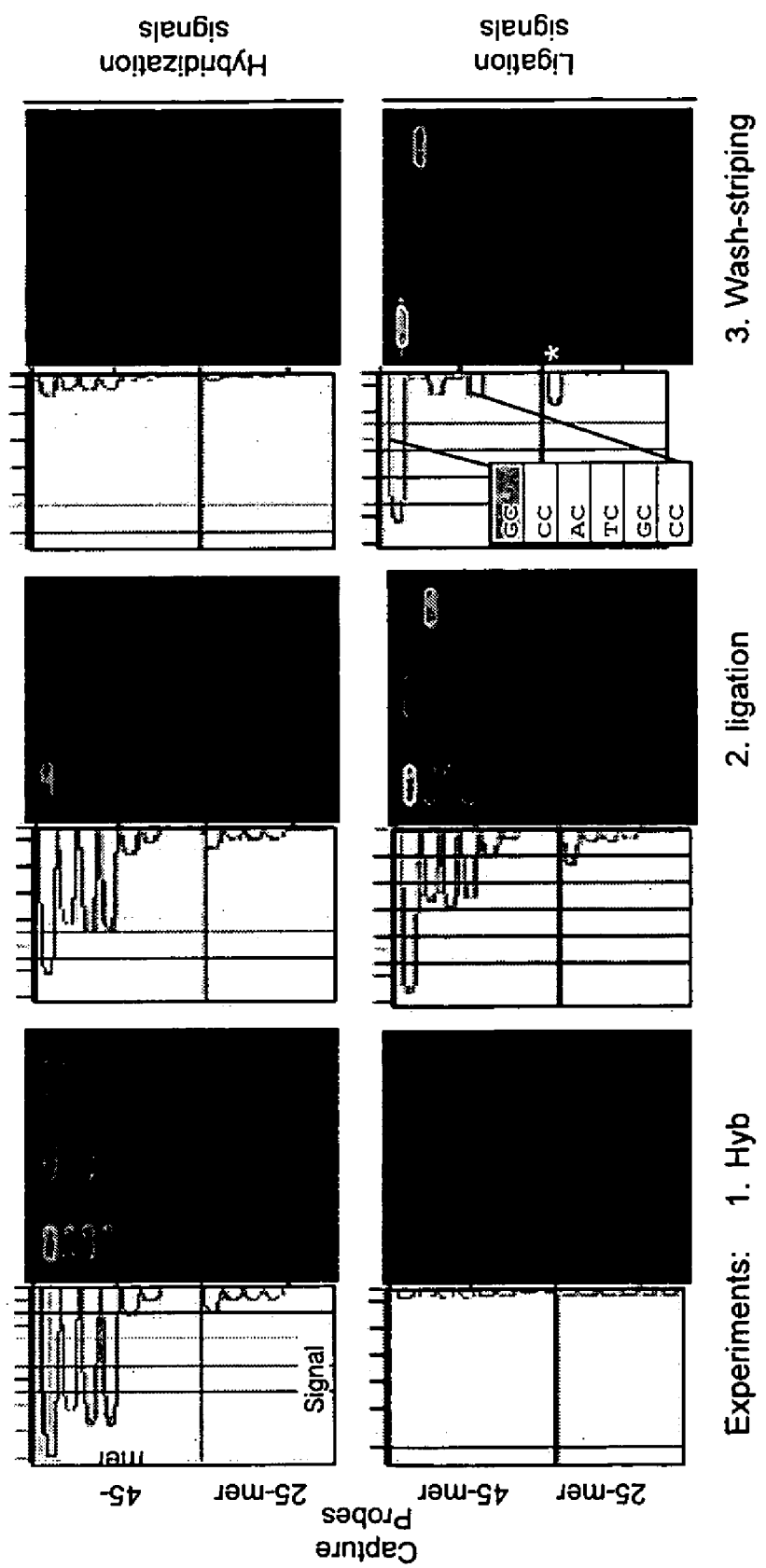
FIG. 10A-10F—Fluorescence images showing cy5 signal detection of: (A) hybridization of cy5-labeled PCR products to chip; (B) the chip after ligation reaction; (c) the chip after applying stripping washing. Fluorescence image showing cy3 signal detection of: (D) the absence of any cy3-labeled sequences; (E) ligation reaction results; (F) the presence of ligated sequences after stripping washing the chip.
Figure 11:
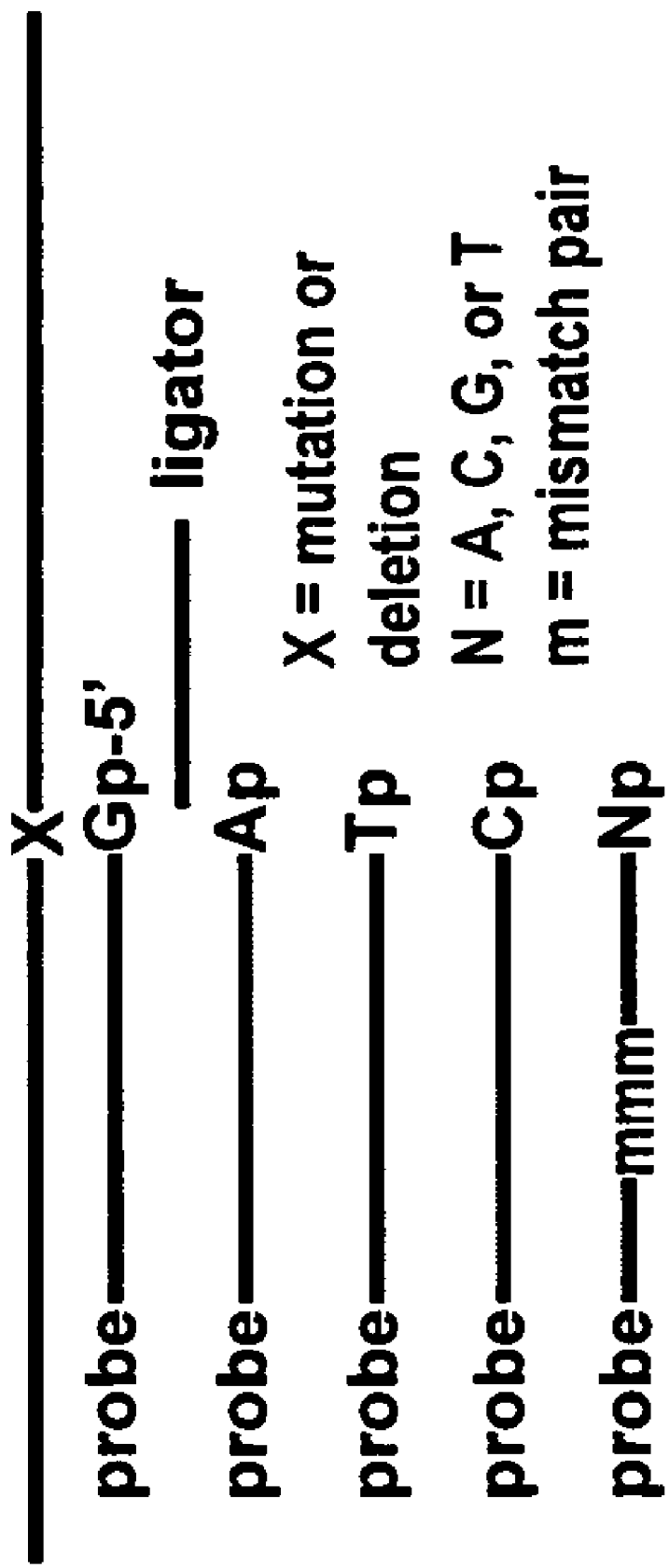
FIG. 11—A schematic illustration of the positive and the negative probes designed for SNP diagnostic tests using ligation.

The present invention also provides methods for detection of sequences of specific terminal sequences (FIG. 10 and FIG. 11). Ligation occurs efficiently when the ligation ends of the capture probe and hybridizing sequence or of the two co-hybridizing sequences form perfect base pairs (C to G and T to A). In one embodiment of the present invention, the capture probe may also be designed to form mismatch at a specific site with the sequences to be detected, such as a SNP site (FIG. 10 and FIG. 11). The mismatch containing capture probe provides positive signal after hybridization but negative signal after ligation and stripping washing of the un-ligated sequences as shown in FIGS. 10 and 11.

Figure 6:
FIG. 6—Illustration of restricted randomization of oligos synthesized on chip. The sequences are written as pseudo-sequences using pseudo-codons. The group # are corresponding to a defined mixture of nucleotides. Each pseudo-codon represents several coding sequences and several amino acid residues; each pseudo-sequence represents a number of oligo sequences and several peptide sequences. The combinations of nucleotide mixtures (groups) and composition of the pseudo-codons may vary from time to time according to the requirement of the protein sequence design.

The present invention provides method for synthesizing multiple sequences within the same reaction site as shown in FIG. 6: The synthesis utilizes single nucleotides and nucleotide mixture groups to generate different sequences at the same reaction site in an array. The nucleotide mixture contains at least two or more different types of nucleotides and its incorporation into the synthesis of oligos produce a mixture of sequences. Trinucleotide codons are often used as a unit for randomization in the generation of protein or peptide coding sequences. There are 61 codons for expression of 20 natural amino acid and there are 20 preferred codons for protein expression in $E.\ coli$ (FIG. 6. Example codons). The methods of the present invention can be used to synthesize a library of protein sequences. The corresponding DNA sequences are written as pseudo-sequences using pseudo-codons. The group number corresponds to a defined mixture of nucleotides. Each pseudo-codon represents several coding sequences and several amino acid residues. Each pseudo-sequence represents a number of oligo sequences and several peptide sequences. The combinations of nucleotide mixtures (groups) and composition of the pseudo-codons may vary from time to time according to the requirement of the protein sequence design and the synthesis. As illustrated in FIG. 6, nine pseudo-codons (a through i) represent all 20 natural amino acids and do not include stop codons. The selection of five pseudo-codons for synthesis of the DNA sequences in a region coding for seven amino acids results in 78,125 pseudo sequences containing predetermined pseudocodons, which represent 62,748,517 individual sequences of natural nucleotides and grouped by the pseudo-codon arrangement in a sequence. The prescribed method of randomization in the synthesis is referred as restricted randomization (rRAM). The design of different combinations of pseudo-codons for synthesis of an array of oligo mixtures determines the generation of large sequence libraries.

The methods of the present invention provide for the synthesis of oligo mixtures using the rRAM method. The oligos may be cleaved from surface using the methods known in the art (e. g. Gao et al. 2003) and used in ligation for making long sequences as previously described herein.

Figure 7:
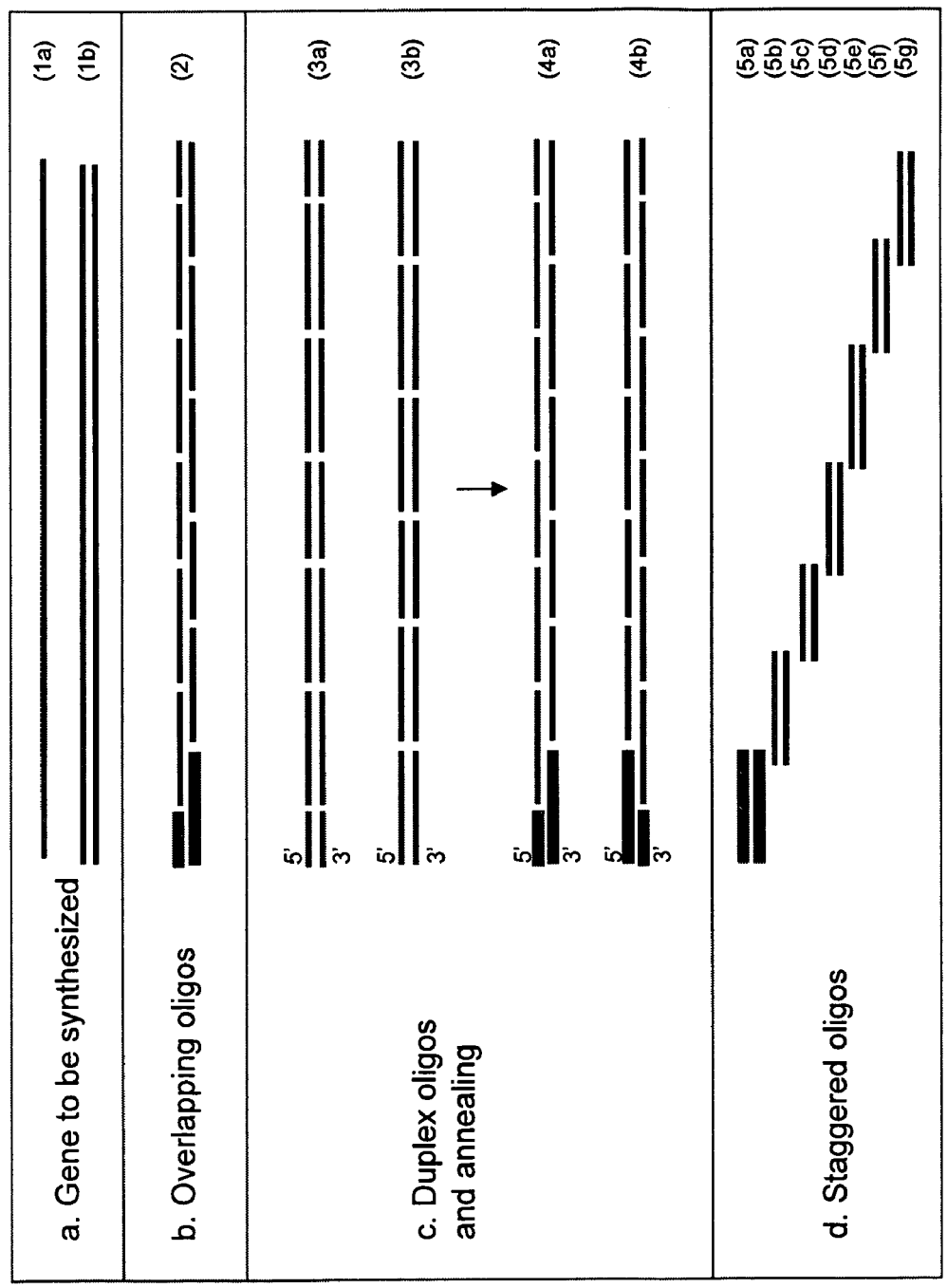
FIG. 7—Illustration of long DNA synthesis by hybridization and ligation of a set of oligos. The number of oligos is determined according to the length of the gene to be synthesized. When assembling on solid surface, the capture probes are indicated on left of the sequence drawing by thicker lines. The synthesis may directly reach the full length of the gene, or several fragments of the gene will be assembled first and these fragments are then assembled to give the full length gene (FIG. 7B). The lengths of oligos are generally 6-100 residues and preferably 25-70 residues. Duplexes may be directly synthesized or are PCR products, which may need to be treated with restriction enzymes for removal of primer sequences which are not part of the genes to be assembled. (a) The genes to be synthesis may be either single or double strands. (b) An oligo set contains sequences which are designed as partially overlapping duplexes. Hybridization and ligation to join these sequences produces long DNA sequence. (c) Two sets of oligo duplexes are designed as partially overlapping duplexes. The end of these duplexes may be blunt or contains overhand sequences. Hybridization and ligation to join these sequences produces long DNA sequence. (d) An oligo set contains sequences which are designed as partial overlapping duplexes. DNA amplification reaction extends the overlapping duplexes into a full-length duplex.
Figure 8:
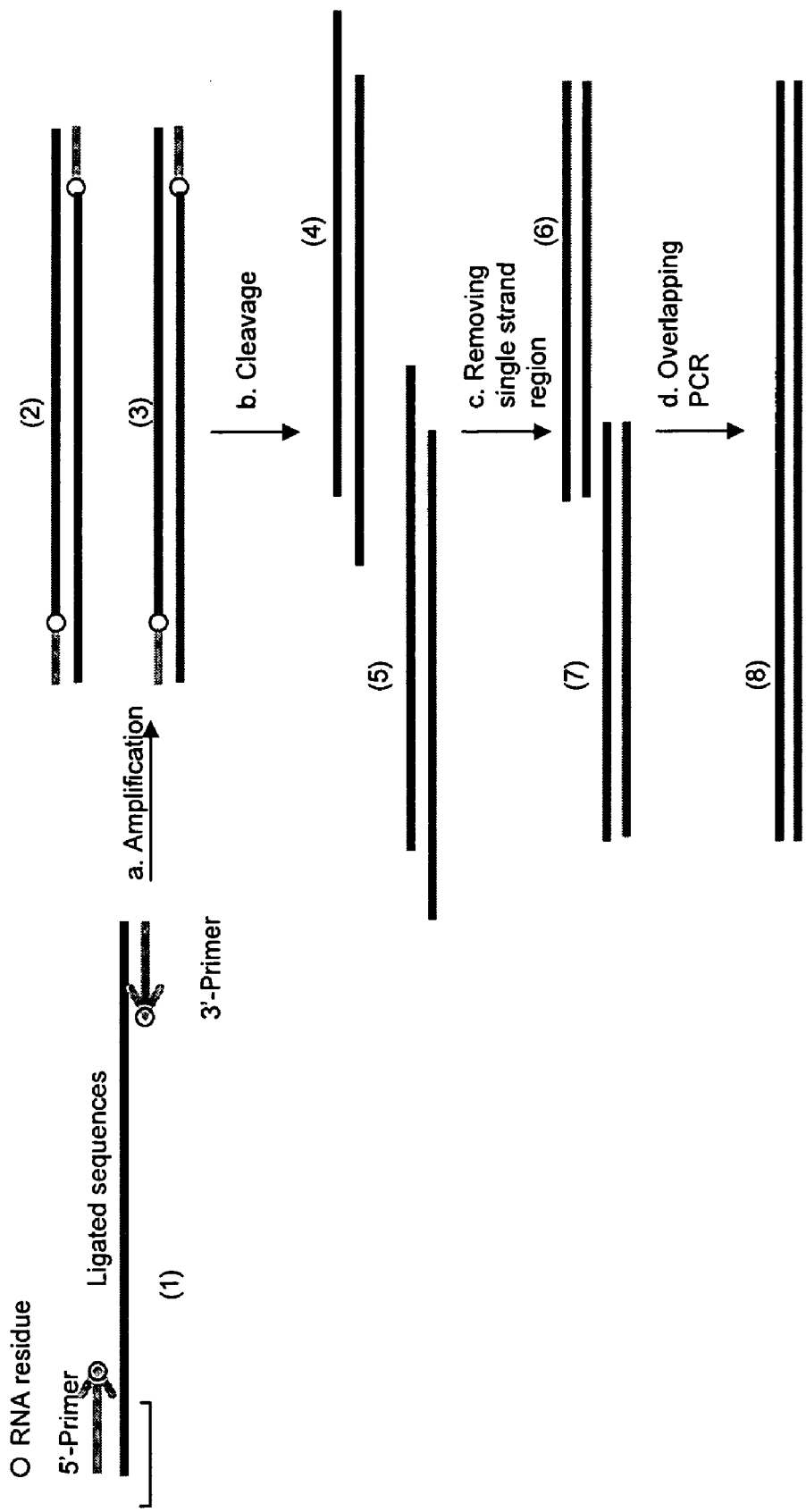
FIG. 8—Illustration of long DNA synthesis using ligated DNA fragments and the corresponding DNA primers or primers containing RNA residues. The ligated DNA fragments to be assembled are not limited to two as shown; multiple fragments of ligated DNA or any other DNA duplexes of the suitable sequences may be used to generate longer DNA sequences by overlapping PCR. (a) Having ligated sequences in single strands or duplexes and primers containing RNA residues at the position of cleavage, and performing amplification reactions. (b) Using RNase enzyme to cleave the RNA bonds. (c) Using single strand DNA nuclease to digest the dangling ends formed after removal of the primers. (d) Performing overlapping PCR to produce long DNA.

The present invention demonstrates long DNA synthesis by hybridization and ligation of a set of oligos using the strategies listed in FIG. 7. The number of oligos may be determined according to the length of the gene to be synthesized. The capture probes are indicated by thicker lines on the left of the sequence drawing. The synthesis may complete the full length of the gene, or alternatively several fragments of the gene may first be assembled and these fragments can then assembled to generate the full length gene (FIG. 8). The lengths of oligos are generally 6-100 residues, preferably 15-80 residues and more preferably 25-70 residues. Duplexes may be directly synthesized or produced as PCR products, which may need to be treated with restriction enzymes for removal of primer sequences which are not part of the genes to be assembled. The strategies of long DNA sequences may include:

(a) The genes to be synthesized may be either single or double strands.

(b) An oligo set may contain sequences that are designed as partially overlapping duplexes. Hybridization and ligation to join these sequences produce long DNA sequence.

(c) Two sets of oligo duplexes may be designed as partially overlapping duplexes. The end of these duplexes may be blunt or contains overhanging sequences. Hybridization and ligation to join these sequences produces long DNA sequence.

(d) An oligo set contains sequences that are designed as partial overlapping duplexes. DNA amplification reaction extends the overlapping duplexes into a full-length duplex.

The methods of the present invention can be used for the synthesis of DNA for generation of protein libraries containing more than ten different protein sequences and potentially up to $10^{16}$ different proteins. The ligated DNA sequences obtained from on-surface ligation may be directly cloned or cloned after amplification into an expression vector. In case of amplification, the primer regions can be removed from the amplified products by restriction enzymes. (Tian et al. 2004). Alternatively, primers containing RNA residues at the designed cleavage site may be used for primer region removal as shown in FIG. 8. Long DNA synthesis may use ligated oligos and primers containing RNA residues. The ligated DNA sequences are not limited to two as shown in FIG. 8 and multiple fragments of ligated DNA or any other DNA duplexes of the suitable sequences may be used to generate longer DNA sequences by having ligated sequences in single strands or duplexes and primers containing RNA residues at the position of cleavage, and performing amplification reactions; using RNase enzyme to cleave the RNA bonds; using single-strand DNA nuclease to digest the dangling ends formed after removal of the primers; performing overlapping PCR to produce long DNA. Alternatively, a restriction enzyme cleavage site may be engineered for removal of the primer sequence after amplification (FIG. 8a). Performing overlapping PCR produces long DNA.

The present invention provides methods for generating subset(s) of oligo mixtures from a larger number of oligo sequences. The subsets of sequences contain signature priming regions. The subsequent amplification reaction as shown in FIG. 8a or as the PCR reaction well-known to those skilled in the field in separate reaction containers in the presence of the specific primers provides subsets of the sequences as designed.

Figure 9:
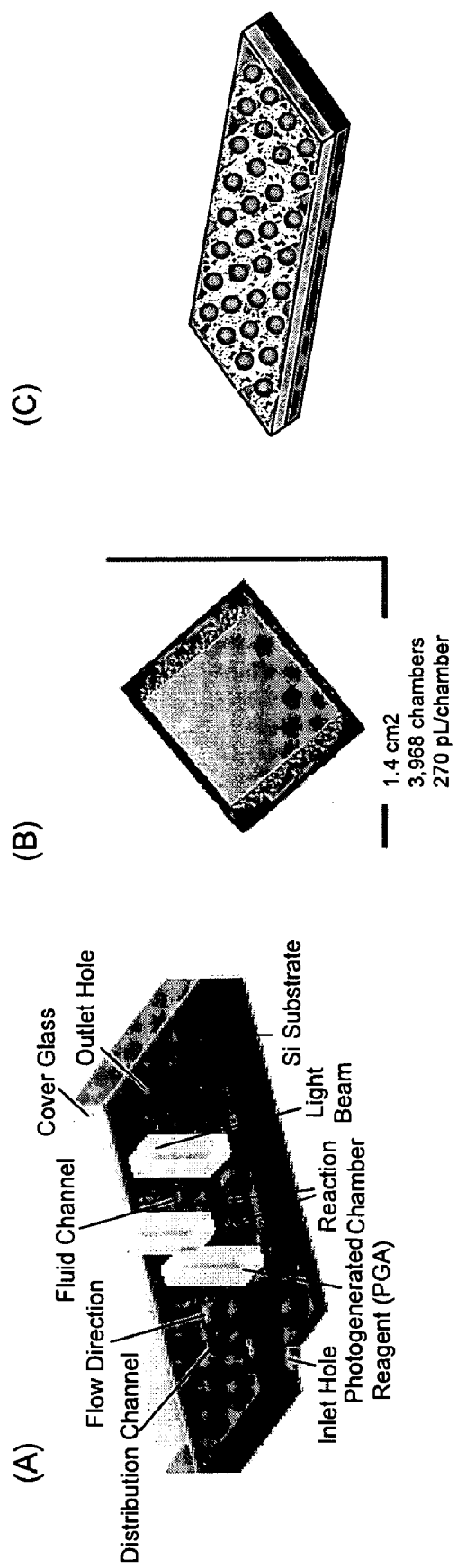
FIG. 9A—Schematic illustration of a microchip for parallel synthesis, hybridization, ligation, and other enzymatic reactions of oligonucleotides and of products of these reactions. A two layer structure consists of annealed silicon and glass, isolated reaction chambers etched on silicon and aligned in parallel and inlet and outlet solution distribution channels that are connected through reaction chambers. The digital light projection is shown at selected sites to allow photogenerated acid-controlled reaction to occur only in light-irradiated reaction chambers. The subsequently hybridization, ligation, and other reactions are carried out on the same surface; else the oligos are synthesized and cleaved and the oligo mixture is applied to another microchip containing capture probes.
FIG. 9B—Illustration of the dimensions of a physical microchip for the described synthesis of oligo mixture. The chip is also used for demonstration of hybridization, ligation and other enzymatic reactions FIG. 9C—Schematic illustration of a flat surface derivatized with synthesis support for the described synthesis of oligo mixture. The spots are spatially separated reaction sites.

The methods of the present invention include the synthesis, hybridization, and ligation of oligos performed on spatially separated surfaces. The present invention includes ligation reactions carried out in parallel on surface that has a density from at least nine sites per $mm^2$ to about $2.0 \times 10^{11}$ sites per $mm^2$. In a preferred embodiment of the present invention, the reactions are performed using a three-dimensional microfluidic device having the structural features shown in FIG. 9. (Zhou and Gulari, USP Application 20030118486; Zhou et al. 2004). FIG. 9 is a schematic illustration of a microchip containing picoliter reaction chambers for parallel synthesis, hybridization, ligation, and other enzymatic reactions of oligos and of products of these reactions. A two-layer structure of the microchip consists of annealed silicon and glass, isolated reaction chambers etched on silicon and aligned in parallel and inlet and outlet solution distribution channels that are connected through reaction chambers. The digital light projection is shown at selected sites to allow photogenerated acid-controlled reaction to occur only in light-irradiated reaction chambers. The subsequently hybridization, ligation, and other reactions are carried out on the same surface. Alternatively the oligos are synthesized and cleaved and the oligo mixture is applied to another microchip containing capture probes. The present invention provides an illustration of the dimensions of a physical microchip for the described synthesis, hybridization, ligation and other enzymatic reactions in FIG. 9. However, the parallel, miniaturized reactions at separated reactions are not limited to the microfluidic chip described. Other types of surfaces providing spatially separated sites and allowing individual reactions may also be suitable for the described synthesis, hybridization, ligation and other enzymatic reactions.

Figure 12:
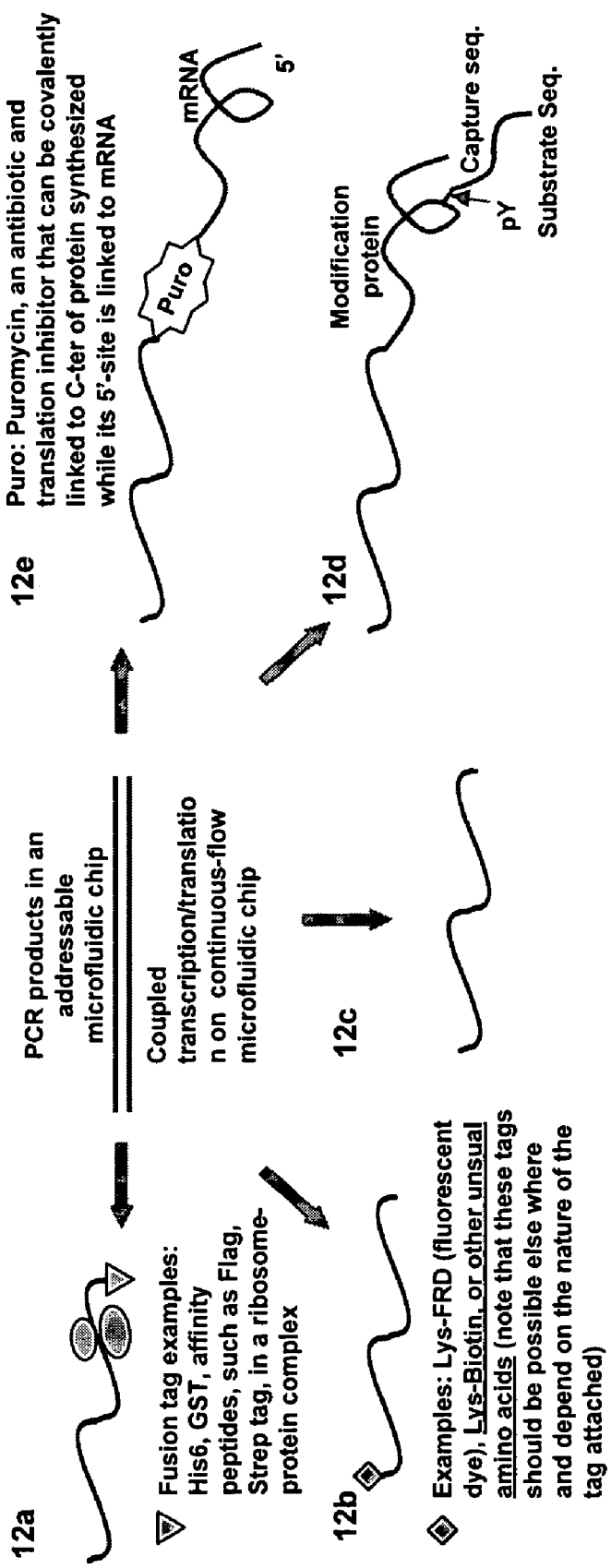
FIG. 12—An illustration of the methods for immobilization of proteins using fusion protein strategy that can be coupled with cell-free protein expression on chip. Proteins of interest are nascent proteins or nascent protein fused with fluorescent protein as in situ expression indicator. (12a) Ribosome or polysome protein complex with affinity tag attached for binding to immobilization surfaces. (12b) Proteins of interest tagged with affinity binding moiety through fusion peptides or unusual amino acid incorporation. (12c) Proteins of interest for direct assays in solutions. (12d) Proteins of interest fused with a modifier protein that is capable to form covalent bond with oligonucleotide sequence which is unique for the protein. (12e) Proteins of interest tagged with puromycin which is also covalently linked to the coding mRNA of the protein.

The present invention also utilizes three dimensional microfluidic microchip technologies to enable the manufacture of long segments of nucleic acids inexpensively and efficiently. Such microfluidic microchip devices and synthesis methods are described in US Patent Publication No. 20020012616, US Patent Publication No. 20030118486 and US Pat. No. 6,426,184 which are incorporated by reference. The long nucleic acid sequences, especially the long DNA sequences, are synthesized as described in FIGS. 1, 2, 3C, 4-8. However, the surface and surface immobilized capture probes used for making long DNA sequences are not limited to those produced by the synthesis methods described herein, and these may be obtained by spotting of pre-synthesized oligos. The long DNA synthesized may be designed to contain the RNA synthesis promoter site, such as T4 or T7 promoter sequence, and be retained on surface as the template strand confined in individual reaction sites for RNA synthesis. These long DNA sequences immobilized on surface may be treated with in vitro transcription reaction conditions for making RNA sequences or in vitro translation reaction conditions for cell-free protein synthesis. These reaction kits are available from various commercial sources. The individual reaction sites on the microfluidic microchip are miniaturized microtiter, nanotiter, picotiter, attotiter plates, on which protein microarray may be created using the immobilization strategies shown in FIG. 12, wherein immobilization is achieved by making fusion proteins and the affinity tag such as epitope peptides, puromycin, and RNA in the fusion protein cause protein to bind to the surface. These methods of protein immobilization are well known to those skilled in the field. The present invention provides method for massively parallel reactions of protein production and protein arraying in a high throughput mode. The protein on-chip expression is optimized by varying on surface the media conditions, the temperature, the time for protein growth, and several other factors.

The method of the present invention is used to manufacture long segments of DNA inexpensively and efficiently. The general scheme of the methods of the present invention can be seen in FIG. 2. In one embodiment of the present invention, in the first step, capture probes are synthesized on a solid support containing a plurality of reaction sites for the synthesis (FIG. 2, species 1). Target oligos that is in part complementary to the capture probe are added to the capture probes on surface and hybridized to the capture probes under specific hybridization conditions (FIG. 2, species 2). An oligo mixture of ligators is added to the hybridizing capture probe and target oligo and the ligators are in part complementary to the target. Duplexes are formed that contain a nick site and the ligator oligos contain an overhang region of single-stranded sequence (FIG. 2, species 3). The two ends of the capture probe and the ligator are then ligated by the addition of ligase under appropriate conditions. As can be seen in FIG. 2, the steps of adding another target oligo or ligator, hybridization of ligator to the single-stranded region of the ligated sequence (FIG. 2, species 5 and 9), ligation of ligator to ligated sequences provides long duplex DNA (FIG. 2, species 6 and 8). As illustrated in FIG. 2, alternative methods of oligo assembling of long DNA sequences in single strands or duplexes are possible. These ligation products can be subjected to amplification and fusion PCR to produce full-length gene sequences as shown in FIG. 8.

Figure 13:
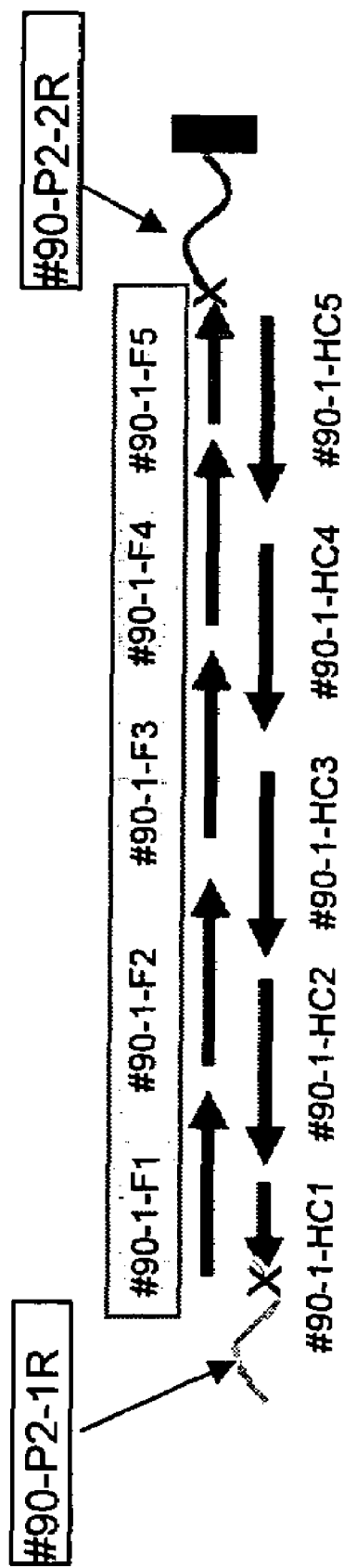
FIG. 13—Oligonucleotide arrangement of the 268 bps DNA fragment (SEQ ID #90-1) for assembly by hybridization and ligation to give long DNA constructs. Multiple fragments will be assembled simultaneously. The assembled sequences can be amplified using primers such as those shown as SEQ ID #90-P2-1R and #90-P2-2R. "x" is a restriction enzyme recognition site.

The present invention also encompasses a length-dependence test for step-wise monitoring of DNA assembling on chip as depicted in FIG. 13. The oligos attached to the chip surface through a 3'-primer are called capture-oligos and the oligos for hybridization and ligation are ligation-oligos. All the sequences use the same monitoring sequence, i.e., a 5'-cy3 labeled detection-oligo, which was made separately from the regular CPG support. The lengths of the ligation-oligos are ~41 nucleotides (nts) and the number of the oligos in FIG. 13 is only representative and varies from sequence to sequence.

The stepwise reaction (one step for 2-piece assembling, two steps for 3-piece assembling (FIG. 13) involving increasing-length hybridization and ligation gives from 20-40% yield under the conditions described in Example 2. Factors affecting these reactions such as DNA topology, ologonucleotide concentration, temperature and pH may be optimized to increase the yield. In particular, compounds that promote condensation of DNA may be particularly effective in increasing yield may be included in the buffer used in hybridization and/or ligation reactions. Such condensation promoting compounds include but are not limited to poly-L-lysine, polyethyleneglycol (PEG), polyethyleneimine (PEI), cationic compounds, DNA binding agents, and chelating agents. Alternatively, the use of agents that promote decondensation or generally affect DNA topology may also be effective in increasing yield and may be used sequentially or in combination with condensation agents. The microfluidic nature of the capture chips is especially useful for the addition and washing away of compounds that may promote condensation or decondensation so that the optimal yield may be achieved.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, genetics, chemistry or related fields are intended to be within the scope of the following claims.

EXAMPLES

The following examples are included to demonstrate embodiments of the invention. It should be appreciated by those of skill in the art that the techniques disclosed in the examples are representative techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Materials

DNA oligonucleotides microfluidic chips were synthesized as described in our previous publication (Zhou et al. Nucleic Acids Res. 32, 5409-5417 (2004)). Restriction Enzymes MlyI, BbsI, BsaI, VentR® DNA Polymerase, Taq DNA ligase and T4 DNA ligase were purchased from New England Biolabs. TOPO TA Cloning® Kit for Sequencing containing pCR4-TOPO vector and Oneshot® TOP 10 Chemically Competent E. Coli was purchased from Invitrogen. CPG oligonucleotides for the EGFP gene (gi:7638256, 712 nts) were purchased from Integrated DNATechnologies. QIAquick Nucleotide Removal Kit, PCR Purification Kit and Gel Extraction Kit, and QIAprep Spin Miniprep Kit were purchase from QIAGEN Inc.

Example 1

On Surface Ligation

The images shown in FIG. 10 demonstrate the results of on surface ligation using template strands synthesized on CPG and ligators synthesized using microchip (Zhou et al. 2004). The experiment used the target sequences (SEQ ID #4180-#4183) from cystic fibrosis transmembrane conductance regulator (CFTR) gene. These four 81-mer DNA sequence targets were amplified by PCR on DNA products made from chip-synthesized oligos. SEQ ID #4180 corresponds to the portion of the wild-type CFTR gene between 1069-1089. SEQ ID #4181 corresponds to a C to G mutation of this wild-type fragment at position 1650. SEQ ID #4182 corresponds to a C to G mutation of this wild-type fragment at position 1655. SEQ ID #4183 corresponds to a mismatch (MM) mutation (deletion) of this wild-type fragment at sites 1652-1654. The mutations were interrogated by synthesizing 34 capture probes in lengths of 35-mers and 25-mers, which incorporated A, C, G, or T at the 5'-position of the capture probes and ligators which were 15-mers that were complementary to target sequence on the 3'-side of the capture probes as illustrated in FIG. 11. Hybridization of a target sequence to the capture probes was carried out on the chip using a microperistaltic pump to circulate 100 µl sample solution. Hybridization buffer solution was 6×SSPE with 25% formamide (for hybridization) or 1×SSPE with 25% formamide (for stringent post-hybridization wash). The temperature of the chip was controlled by a Peltier heating/cooling plate adjusted 32° C. The hybridization image was acquired using laser scanner (GenPix 4.0, Axon) (FIG. 10A and 10D). Ligation was 4 hrs at 45° C. and used 45 µl solution (20 mM Tris-HCl (pH 7.6), 25 mM potassium acetate, 10 mM magnesium acetate, 10 mM dithiothreitol, 1 mM NAD, 0.1% Triton X-100, 15% PEG-8000, 10% DMSO), 20 U Taq DNA ligase. Ligation reactions were run for four hours or longer and the surface was then washed with 1×SSPE with 25% formamide and the ligation image of the chip was taken (FIG. 10B and 10E). Finally, the surface was washed with water at 50° C. and the after-washing image was taken (FIG. 10, images of the last column).

Example 2

Oligonucleotide Design for Long DNA Synthesis:

All sequences discussed in this example are listed in Table 1. A 1 kb long DNA (SEQ ID #90) is divided into four 268 bps fragments (SEQ ID #90-1 to #90-4) with the first fragment (SEQ ID #90-1) 3'-end overlapping with 5'-end of second fragment (SEQ ID #90-2), and 3'-end of second fragment overlapping with 5'-end of third fragment (SEQ ID #90-3) and so on. For each 268 bps fragment, it is divided into two sets of oligos. One set of these oligos contains SEQ ID #90-1-F1 to #90-1-F5 (FIG. 13), SEQ ID #90-2-F1 to #90-2-F5, #90-3-F1 to #90-3-F5 and #90-4-F1 to #90-4-F5; the other set contains SEQ ID #90-1-H1 to #90-1-H5, #90-2-H1 to #90-2-H5, #90-3-H1 to #90-3-H5 and #90-4-H1 to #90-4-H5. Two sets of oligos are from the same strand of 1 kb long DNA (SEQ ID #90). The lengths of these oligos are as such that SEQ ID #90-1-F1 is half overlapping with SEQ ID #90-1-H1, and SEQ ID #90-1-H2 is half overlapping with SEQ ID #90-1-F1 and SEQ ID #90-1-F2 and so on. The complementary strand of the 1 kb long DNA (SEQ ID #90-C) is also divided into four 268 bps fragments (SEQ ID #90-C1 to #90-C4). For each 268 bps fragment, it is divided into two sets of oligos using the same strategy mentioned above, containing SEQ ID #90-1-FC1 to #90-1-FC5, SEQ ID #90-2-FC1 to #90-2-FC5, #90-3-FC1 to #90-3-FC5 and #90-4-FC1 to #90-4-FC5; the other set contains SEQ ID #90-1-HC1 to #90-1-HC5, #90-2-HC1 to #90-2-HC5, #90-3-HC1 to #90-3-HC5 and #90-4-HC1 to #90-4-HC5.

The length considerations of oligos include PCR efficiency, hybridization affinity and uniformity of the distribution for the numbers of each oligonucleotide.

Example 3

EGFP Oligos as Assembly Control

Figure 14A:
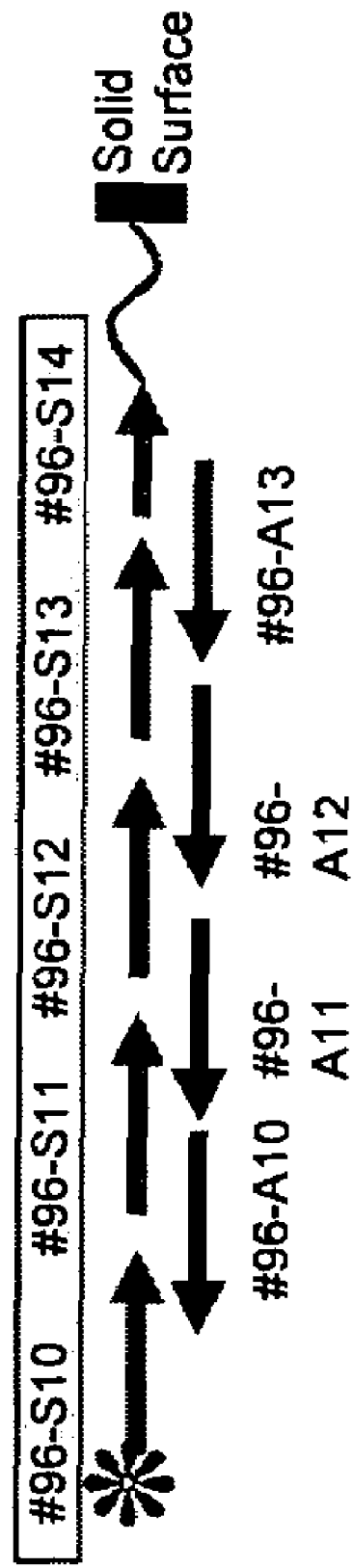
FIG. 14A—Illustration of oligonucleotide layout of an EGFP fragment. The length of oligos were around 40 residues. SEQ ID #96-S10 is 5'-labeled with cy3 dye.

The EGFP oligonucleotides #96-A10 to #96-A13 are the complementary sequences of #96-S10 to #96-S13, repectively (FIG. 14). The arrangement of these oligoes is as such that SEQ ID #96-A10 is half overlapping with SEQ ID #96-S10 and #96-S11, and SEQ ID #96-A11 is half overlapping with SEQ ID #96-S11 and SEQ ID #96-S12 and so on (FIG. 14A). The 5'-end of SEQ ID #96-S10 was labeled with fluorescent dye Cy3.

Example 4

Generation of Oligos for Solution Assembly

SEQ ID #90-P1-1F (5'-CACAGGAGTCCTCAC) and SEQ ID #90-P1-2R (5'-CTAGCGACTCCTTGG) containing a endonuclease restriction site, MlyI (5'-GAGTC(N5)/-3'-CTCAG(N5)) where N is A, C, G, or T were added to the 5'- and 3'-end of the oligos for each of the 268 bps fragments (SEQ ID #90-1, #90-2, #90-3, and #90-4) (Table 1) as described in Example 2 and these oligos were synthesized on a DNA microchip as described (Zhou et al. Nucleic Acids Res. 32, 5409-5417 (2004)). The synthesized oligos were cleaved from the chip using concentrated aqueous ammonia hydroxide at 55° C., 18 hrs. After evaporating ammonia from the solution, the cleaved oligos were precipitated in 80% ethanol/water, and the precipated oligos were re-dissolved in 25 µL water. The oligonucleotides was amplified using polymer chain reaction (PCR) and a 25 µL reaction contained: 1 µL of the oligons cleaved from synthesis chip, primers (SEQ ID #90-P1-1F and SEQ ID #90-P1-2F), 1 U of vent DNA polymerase; 200 µM dNTPs; and 1× ThermoPol Reaction Buffer. The reaction used 5 min at 94° C., then 25 cycles of 30 sec at 94° C., 40 sec at 60° C., and 2 min at 72° C.; and a final step of 2 min at 72° C., final sitting at 4° C. The PCR product was treated with 10 U restriction enzyme MlyI, 0.5 mg/mL BSA and 1× NEB buffer 4. The reaction was performed at 37° C. for 3 hrs. The reaction solution was passed through a QIAquick Nucleotide Removal column following the procedure provided by the vendor and the oligos were recovered. These oligos are to be used for assembling of long DNA after annealing and ligation and they are called ligators.

Example 5

Generation of Oligos for Solid Surface Assembly

SEQ ID #90-P1-1F (5'- CACAGGAGTCCTCAC) and SEQ ID #90-P 1-2R (5'-CTAGCGACTCCTTGG) containing a endonuclease restriction site, MlyI (5'-GAGTC(N5)/-3'-CTCAG(N5)) where N is A, C, G, or T were added to the 5'- and 3'-end of the oligos except those of the most 3'-end for each of the 268 bps fragments (SEQ ID #90-1, #90-2, #90-3, and #90-4) (Table 1) as described in Example 2 and these oligos were prepared as described in Example 4.

Example 6

Generation of ssDNA Ligators for Solid Surface Assembly.

The oligonucleotides for both strands of each of the 268 bps fragments (SEQ ID #90-1, #90-2, #90-3, and #90-4) as listed in Table 1 except for those at the 3'-end of the fragments (SEQ ID #90-1-F1 to #90-1-F4, SEQ ID #90-2-F1 to #90-2-F4, #90-3-F1 to #90-3-F4, #90-4-F1 to #90-4-F4, SEQ ID #90-1-H2 to #90-1-H5, #90-2-H2 to #90-2-H5, #90-3-H2 to #90-3-H5 and #90-4-H2 to #90-4-H5; SEQ ID #90-1-FC1 to #90-1-FC4, SEQ ID #90-2-FC1 to #90-2-FC4, #90-3-FC1 to #90-3-FC4, #90-4-FC1 to #90-4-FC4, SEQ ID #90-1-HC2 to #90-1-HC5, #90-2-HC2 to #90-2-HC5, #90-3-HC2 to #90-3-HC5 and #90-4-HC2 to #90-4-HC5) were synthesized on a DNA microchip as described (Zhou, 2004). The synthesized oligos were cleaved from the chip using concentrated aqueous ammonia hydroxide at 55° C., 18 hrs. After evaporating ammonia from the solution, the cleaved oligos were precipitated in 80% ethanol/water, and the precipated oligos were re-dissolved in 50 µL water.

Example 7

Preparation of Capture Probes on Solid Surface

SEQ ID #90-P2-1R was added to oligos (SEQ ID #90-1-F5, #90-2-F5, #90-3-F4, #90-4-F5, #90-1-H5, #90-2-H5, #90-3-H5 and #90-4-H5) and SEQ ID #90-P2-2F was added to oligos (SEQ ID #90-1-HC1, #90-2-HC1, #90-3-HC1 and #90-4-HC1, #90-1-FC1, #90-2-FC1, #90-3-FC1, #90-4-FC1) of each of the 268 bps DNA fragments. These oligos were synthesized on a DNA microchip and the 5'-end OH was phosphophorylated using phosphorylation agent from Glen Research as described (Zhou, 2004). This chip is called capture chip and oligos contained on the chip are called capture oligos. The quality of the chip was monitored by an established procedure involving hybridization of fluorescence labeled oligo to the probes on chip. The surface was scanned using a laser scanner to obtain images and the intensities of the fluorescent signals were used as criteria for chip synthesis quality.

Example 8

Assembly Multiple DNA Fragments on Solid Surface

A mixture of the ligators as described in Examples 5 and 6 in 200 µL hybridization solution (6×SSPE, 25% formamide, 0.2% BSA, pH 6.5) was applied to a capture chip using a peristaltic micropump at 30° C. and the solution was circulated for 12 hrs. The hybridization ligator solution was replaced by a stringent wash solution (1×SSPE, 25% formamide, 0.2% BSA, pH 6.5) and the surface was washed for 10 min. The chip was then filled with 1× T4 DNA ligase buffer containing 0.4 mg/mL BSA (NEB) with circulation of 150 µl of the ligaton buffer. Ligation on the chip used 150 µl T4 ligation solution (400 U T4 ligase, 1× T4 ligase buffer) at 16° C. overnight. The surface was then washed with 500 µl solution (1×SSPE, 25% formamide, pH 6.5).

Figure 14B:
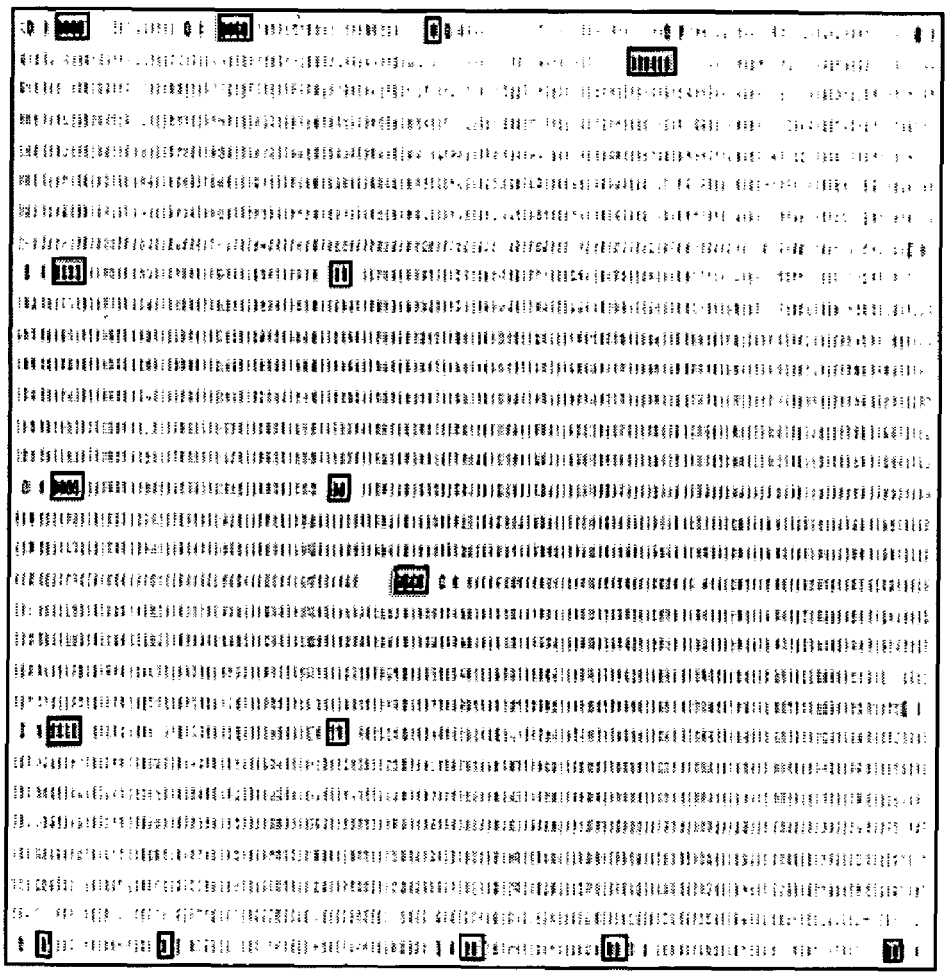
FIG. 14B—Fluorescent image for monitoring the hybridization and annealing of ligators on chip for multiplex assembling of DNA fragments on a surface. The fluorescent signals in boxed regions are due to cy3-labeled SEQ ID #90-S10 and positive signals indicate the desired EGFP DNA fragment is assembled on the surface FIG. 15—Gel image of the EGFP DNA fragment assembled on surface and synthesized using PCR with primers SEQ ID #90-S1 and #90-A14. Lanes 2-4, amplified DNA fragment assembled on solid surface. Lanes 5-7, amplified DNA fragment assembled in solution. Lane 8, molecular weight Marker.

For monitoring hybridization annealing and ligation, a chip image was taken using a laser scanner. The cy3-labeled oligo (SEQ ID #96-S10) in 150 µl hybridization solution was then added and hybridization was done at 30° C. for 12 hrs. The chip was washed with water at 50° C.; an image was obtained using a laser scanner and a representative image is shown in FIG. 14B.

Example 9

Assembly Multiple DNA Fragments in Solution

A ligator mixture as described in Example 3 and 4 in Taq DNA ligase buffer (NEC) containing 40 U Taq DNA ligase in a microtube was placed in a thermal cycler (MJ Research). The temperature cycle was 5 min at 94° C., then 40 cycles of 60 s at 72° C., and 5 min at 45° C; the final temperature was 4° C.

Example 10

Amplification of Assembled DNA Fragments

The assembled DNA fragments on solid surface as described in Example 8 were cleaved using concentrated aqueous ammonia hydroxide at 55° C., 18 hrs. After evaporating ammonia from the solution, the cleaved oligos were precipitated in 80% ethanol/water, and the precipated oligos were re-dissolved in 25 µL water.

The assembled DNA fragments in solution as described in Example 9 were in water.

Figure 15:
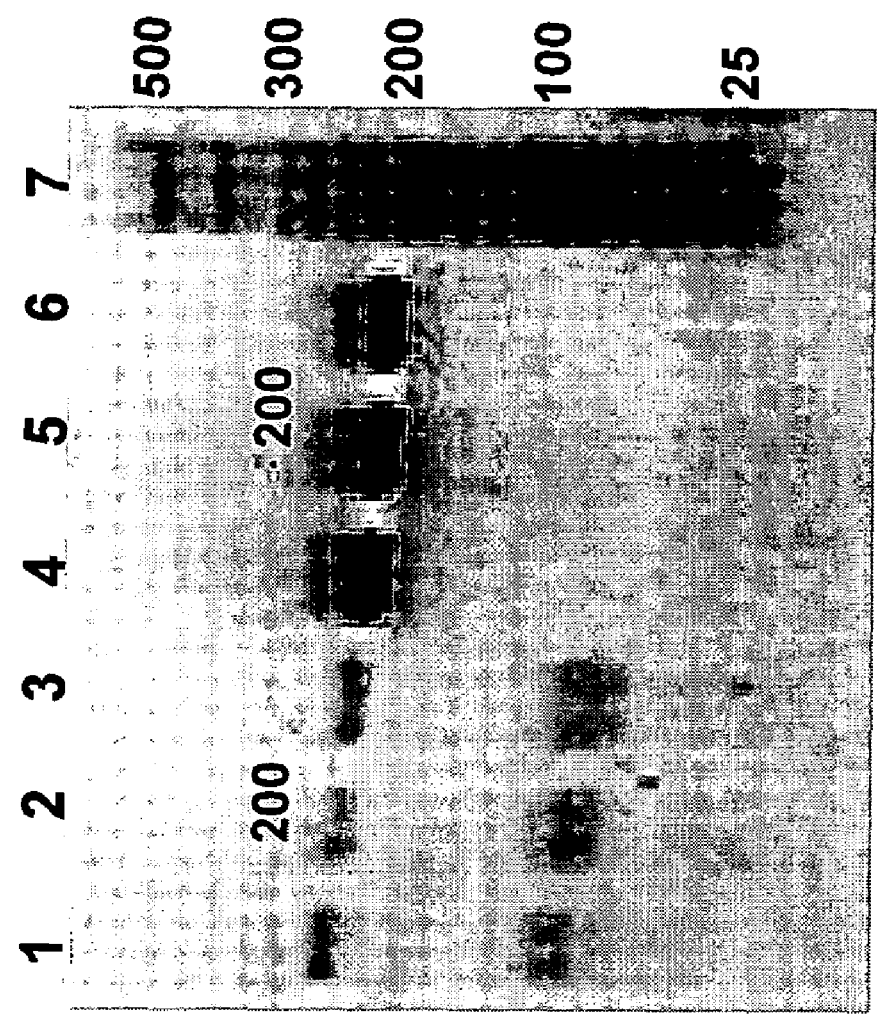

The second primer set (SEQ ID #90-P1-1F and #90-P2-1F) containing the restriction enzyme BbsI recognition cleavage site were used to amplify the DNA fragments assembled using PCR (1 U vent DNA polymerase, 200 µM dNTPs, 1× ThermoPol Reaction Buffer (NEB)). The reaction used 5 min at 94° C., then 25 cycles of 30 sec at 94° C., 40 s at 50-60° C. gradient temperature and 2 min at 72° C., and a final step of 7 min at 72° C., and final at 4° C. The PCR products were purified using a QIAquick PCR Purification Kit according to the manufacturer's instructions. FIG. 15 shows the EGFP DNA fragment (200 bps) assembled from oligos synthesized on chip.

Example 11

1 kb Long DNA (SEQ ID #90) Synthesis

The 268 bps DNA fragments such as SEQ ID #90-1 to #90-4 were treated with 10 U of BbsI (NEB) in 1× NEB buffer 2. The reaction was performed at 37° C. for 3 hrs, and then purified with a QIAquick Nucleotide Removal Kit according to the manufacturer's protocols.

This mixture of four DNA fragments was added to a 50 µL primer extension and PCR amplification reaction solution containing 5'- and 3'-primers of 1 kb long DNA with a BsaI recognition site (SEQ ID #90-P3-1F and SEQ ID #90-P3-1 F), 1 U of vent DNA polymerase, 200 µM dNTP, and 1× ThermoPol Reaction Buffer. The extension and amplification reaction was performed using 5 min at 94° C., then 25 cycles of 30 sec at 94° C., 40 sec at 56° C., and 2 min at 72° C., and a final step of 7 min at 72° C., final 4° C. The correct size of the 1 kb PCR product was verified by electrophoresis in a 1% agarose gel and 1 kb fragment was obtained using a QIAquick Gel Extraction Kit according to the manufacturer's instructions.

Example 12

Cloning and Sequencing the Assembled DNA Sequences.

Figure 16:
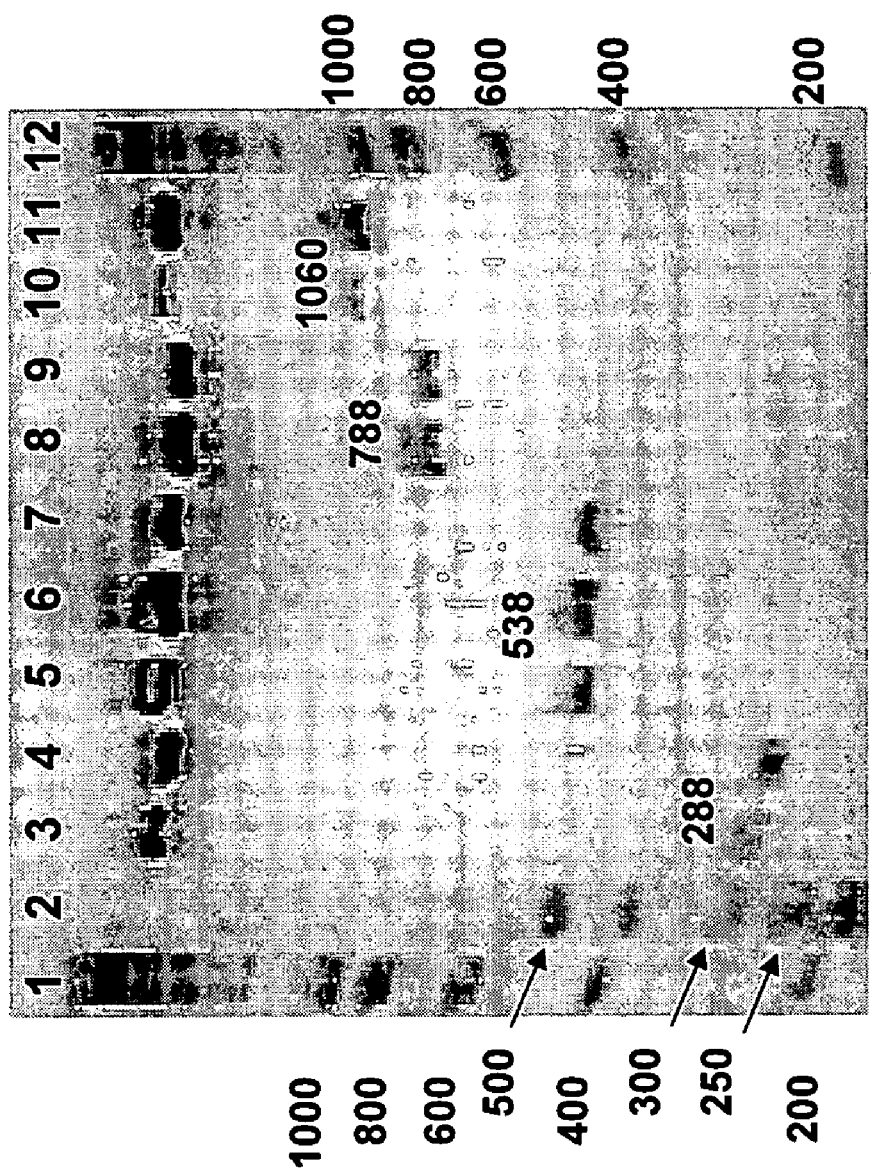
FIG. 16—Intermediate length of DNA fragments and 1 k bps from plasmid after restriction enzymatic (EcoRI) cleavage. Lanes 3 and 4, 268+18 bps DNA fragments; lanes 5, 6 and 7, 520+18 bps DNA fragments, Lanes 8 and 9, 770+18 bps DNA fragments; Lanes 10 and 11, 1,000+42 bps DNA full-length DNA; Lanes 1, 2 and 12, molecular weight markers.

The assembled DNA sequences were PCR amplified (FIG. 16), cloned, and sequenced. The vector inserts were further verified by PCR, restriction enzymatic cleavage (FIG. 16).

TABLE 1

| | Nucleic Acid Sequences |
|---|---|
| #90 | GGTCTTTGTCACCTCCGTCAATTTGTATTAGAACCGTGA
AGGCCCAAGTAACAGGCCCAGGGTTAACATGTACGGAAC
ATACTCCTTCCACGGAAGATTGGGGATGAAAGTTGATAC
CCAAACTTCATTAACACAAAGGCGATGTGGGCCGAGTAC
TGTGCTTACACCAACAGGGCGGCTCAACTGGGTTGGTAG
CCAGCACTAGCTTATTCACAATTAAGGCCGTATGCATTC
TACTGCTTATCCGGTGGTGATTGCAGCCAGGGCGGAAGT
GAACACGCTTGTACGATGTGTTTGCATAAGCGGTTACCA
CAGGCGCTACTCTCGTCGATAGCCGACTACTAATATTCA
GCCGGCGCCGGTAGATAGCGAGGCTTTGGGGGTAGCTTT
AAGTGCGGTCTAGGCTCAGTTGACGATACTTACTTAGGC
AGGGTTACAACCCTTATGATGGGGTATGAGGCACGTGGC
CATTCATCCGGACCCGATGCTGTCGTGCTTCTCGTTGGC
AATAGCGCGGATTAGTACAGGTGACTAGTTCAGCTGTTG
TTCGGATTCCAAGTAAGCTCGCATAGAGCTGGACTTCTC
GGAACGGTCCTGACGCATTCCTGCATCAATACGCGGCAC
CGGGGGTCCGATAGCATCTCGCCTTAGATCCGGCGGGGG
ATACTTGGTCAAAGCTCACTACGGGACTAGAGTGGTAG
TGCAGATGCGCAGCGCAGATATGCTATACGAGATGAGCT
TCAAATTCATGGAGTTATGACGATATAACGCTAGGATCT
GACGCGGTGACACCGGTCGTGTGACAACTGGGCTTTAAG
TGAGGTCTCAGAAGTATACTTTTAATGGTGCCGCTCCCA
AATCCCCGATCTTGCCACGATTGCCTAAGCCGTCATGTT
AGAGGCGGTCACAGCAAACCCCCAGTTTACCGGTTCGAT
GATTATACGATGCCGGAGCGAACGACTACGCTCGAAGTT
TGGTTATCTAGAGCACGTCCG |
| #90-1 | CCTTCCACGGAAGATTGGGGATGAAAGTTGATACCCAAA
CTTCATTAACACAAAGGCGATGTGGGCCGAGTACTGTGC
TTACACCAACAGGGCGGCTCAACTGGGTTGGTAGCCAGC
ACTAGCTTATTCACAATTAAGGCCGTATGCATTCTACTG
CTTATCCGGTGGTGATTGCAGCCAGGGCGGAAGTG |
| #90-2 | AACACGCTTGTACGATGTGTTTGCATAAGCGGTTACCAC
AGGCGCTACTCTCGTCGATAGCCGACTACTAATATTCAG
CCGGCGCCGGTAGATAGCGAGGCTTTGGGGGTAGCTTTA
AGTGCGGTCTAGGCTCAGTTGACGATACTTACTTAGGCA
GGGTTACAACCCTTATGATGGGGTATGAGGCACGTGGCC
ATTCATCCGGACCCGATGCTGTCGTGCTTCTCGTTGGCA
ATAGCGC |
| #90-3 | GGATTAGTACAGGTGACTAGTTCAGCTGTTGTTCGGATT
CCAAGTAAGCTCGCATAGAGCTGGACTTCTCGGAACGGT
CCTGACGCATTCCTGCATCAATACGCGGCACCGGGGGTC
CGATAGCATCTCGCCTTAGATCCGGCGGGGGATACTTGG
TCAAAGCTCACTACGGGACTAGAGTGGCTAGTGCAGATG
CGCAGCGCAGATATGCTATACGAGATGAGCTTCAAATTC
AT |
| #90-4 | GGAGTTATGACGATATAACGCTAGGATCTGACGCGGTGA
CACCGGTCGTGTGACAACTGGGCTTTAAGTGAGGTCTCA
GAAGTATACTTTTAATGGTGCCGCTCCCAAATCCCCGAT
CTTGCCACGATTGCCTAAGCCGTCATGTTAGAGGCGGTC
ACAGCAAACCCCCAGTTTACCGGTTCGATGATTATACGA
TGCCGGAGCGAACGACTACGCTCGAAGTTTGGTTATCTA
GAGCACGTCCGTCTA |
| #90-C | GGTTTGCTGTGACCGCCTCTAACATGACGGCTTAGGCAA
TCGTGGCAAGATCGGGGATTTGGGAGCGGCACCATTAAA
AGTATACTTCTGAGACCTCACTTAAAGCCCAGTTGTCAC
ACGACCGGTGTCACCGCGTCAGATCCTAGCGTTATATCG
TCATAACTCCATGAATTTGAAGCTCATCTCGTATAGCAT
ATCTGCGCTGCGCATCTGCACTAGCCACTCTAGTCCCGT
AGTGAGCTTTGCCAAGTATCCCCCGCCGGATCTAAGGC
GAGATGCTATCGGACCCCCGGTGCCGCTGATTGATGCAG
GAATGCGTCAGGACCGTTCCGAGAAGTCCAGCTCTATGC
GAGCTTACTTGGAATCCGAACAACAGCTGAACTAGTCAC
CTGTACTAATCCGCTATTGCCAACGAGAAGCACGACA
GCATCGGGTCCGGATGAATGGCCACGTGCCTCATACCCC
ATCATAAGGGTTGTAACCCTGCCTAAGTAAGTATCGTCA
ACTGAGCCTAGACCGCACTTAAAGCTACCCCCAAAGCCT
CGCTATCTACCGGCGCCGGCTGAATATTAGTAGTCGGCT
ATCGACGAGAGTAGCGCCTGTGGTAACCGCTTATGCAAA
CACATCGTACAAGCGTGTTCACTTCCGCCCTGGCTGCAA
TCACCACCGGATAAGCAGTAGAATGCATACGGCCTTAAT
TGTGAATAAGCTAGTGCTGGCTACCAACCCAGTTGAGCC
GCCCTGTTGGTGTAAGCACAGTACTCGGCCCACATCGCC
TTTGTGTTAATGAAGTTTGGGTATCAACTTTCATCCCCA
ATCTTCCGTGGAAGGAGTATGTTCCGTACATGTTAACCC
TGGGCCTGTTACTTGGGCCTTCACGGTTCTAATACAAAT
TGACGGAGGTGACAAA |
| #90-C1 | CAACCCAGTTGAGCCGCCCTGTTGGTGTAAGCACAGTAC
TCGGCCCACATCGCCTTTGTGTTAATGAAGTTTGGGTAT
CAACTTTCATCCCCAATCTTCCGTGGAAGGAGTATGTTC
CGTACATGTTAACCCTGGGCCTGTTACTTGGGCCTTCAC
GGTTCTAATACAAATTGACGGAGGTGACAAAGACC |
| #90-C2 | GCGCTATTGCCAACGAGAAGCACGACAGCATCGGGTCCG
GATGAATGGCCACGTGCCTCATACCCCATCATAAGGGTT
GTAACCCTGCCTAAGTAAGTATCGTCAACTGAGCCTAGA
CCGCACTTAAAGCTACCCCCAAAGCCTCGCTATCTACCG
GCGCCGGCTGAATATTAGTAGTCGGCTATCGACGAGAGT
AGCGCCTGTGGTAACCGCTTATGCAAACACATCGTACAA
GCGTGTT |
| #90-C3 | ATGAATTTGAAGCTCATCTCGTATAGCATATCTGCGCTG
CGCATCTGCACTAGCCACTCTAGTCCCGTAGTGAGCTTT
GACCAAGTATCCCCCGCCGGATCTAAGGCGAGATGCTAT
CGGACCCCCGGTGCCGCTGATTGATGCAGGAATGCGTCA
GGACCGTTCCGAGAAGTCCAGCTCTATGCGAGCTTACTT
GGAATCCGAACAACAGCTGAACTAGTCACCTGTACTAAT
CC |
| #90-C4 | TAGACGGACGTGCTCTAGATAACCAAACTTCGAGCGTAG
TCGTTCGCTCCGGCATCGTATAATCATCGAACCGGTAAA
CTGGGGGTTTGCTGTGACCGCCTCTAACATGACGGCTTA
GGCAATCGTGGCAAGATCGGGGATTTGGGAGCGGCACCA
TTAAAAGTATACTTCTGAGACCTCACTTAAAGCCCAGTT
GTCACACGACCGGTGTCACCGCGTCAGATCCTAGCGTTA
TATCGTCATAACTCC |
| #90-1-F1 | GGTCTTTGTCACCTCCGTCAATTTGTATTAGAACCGTGA
AGGCCCAAGTAACAGGCCCAG |
| #90-1-F2 | GGTTAACATGTACGGAACATACTCCTTCCACGGAAGATT
GGGGATGAAAGTTGATACCCAAACTTC |
| #90-1-F3 | ATTAACACAAAGGCGATGTGGGCCGAGTACTGTGCTTAC
ACCAACAGGGCGGCTCAAC |
| #90-1-F4 | TGGGTTGGTAGCCAGCACTAGCTTATTCACAATTAAGGC
CGTATGCATTCTACTGCTTATCCG |
| #90-1-F5 | GTGGTGATTGCAGCCAGGGCGGAAGTG |
| #90-2-F1 | GTGGTGATTGCAGCCAGGGCGGAAGTGAACACGCTTGTA
CGATGTGTTTGCATAAGCGG |
| #90-2-F2 | TTACCACAGGCGCTACTCTCGTCGATAGCCGACTACTAA
TATTCAGCCGGCGCCGG |
| #90-2-F3 | TAGATAGCGAGGCTTTGGGGGTAGCTTTAAGTGCGGTCT
AGGCTCAGTTGACGATACTTACTTAGG |
| #90-2-F4 | CAGGGTTACAACCCTTATGATGGGGTATGAGGCACGTGG
CCATTCATCCGGACCCGATGC |
| #90-2-F5 | TGTCGTGCTTCTCGTTGGCAATAGCGC |
| #90-3-F1 | TGTCGTGCTTCTCGTTGGCAATAGCGCGGATTAGTACAG
GTGACTAGTTCAGCTGTTGTT |
| #90-3-F2 | CGGATTCCAAGTAAGCTCGCATAGAGCTGGACTTCTCGG
AACGGTCCTGACGCATTCC |
| #90-3-F3 | TGCATCAATACGCGGCACCGGGGGTCCGATAGCATCTCG
CCTTAGATCCGGCGG |
| #90-3-F4 | GGGATACTTGGTCAAAGCTCACTACGGGACTAGAGTGGC
TAGTGCAGATGCGCAGCGC |
| #90-3-F5 | AGATATGCTATACGAGATGAGCTTCAAATTCAT |

TABLE 1-continued

Nucleic Acid Sequences

| | |
|---|---|
| #90-4-F1 | AGATATGCTATACGAGATGAGCTTCAAATTCATGGAGTTATGACGATATAACGCTAGGATCTGACG |
| #90-4-F2 | CGGTGACACCGGTCGTGTGACAACTGGGCTTTAAGTGAGGCATCAGAAGTATACTTTTAA |
| #90-4-F3 | TGGTGCCGCTCCCAAATCCCCGATCTTGCCACGATTGCCTAAGCCGTCATGTTAGAGG |
| #90-4-F4 | CGGTCACAGCAAACCCCAGTTTACCGGTTCGATGATTATACGATGCCGGAGCGAACG |
| #90-4-F5 | ACTACGCTCGAACTTTGGTTATCTAGAGCACGT |
| #90-1-H1 | TTCTAATACAAATTGACGGAGGTGACAAAGACC |
| #90-1-H2 | CCGTGAAGGCCCAAGTAACAGGCCCAGGGTTAACATGTACGGAACATACTCCTTCCACGG |
| #90-1-H3 | AAGATTGGGGATGAAAGTTGATACCCAAACTTCATTAACACAAAGGCGATGTGGGCCGAGTACT |
| #90-1-H4 | GTGCTTACACCAACAGGGCGGCTCAACTGGGTTGGTAGCCAGCACTAGCTTATTCAC |
| #90-1-H5 | AATTAAGGCCGTATGCATTCTACTGCTTATCCGGTGGTGATTGCAGCCAGGGCGGAAGTG |
| #90-2-H1 | CACTTCCGCCCTGGCTGCAATCACCAC |
| #90-2-H2 | AACACGCTTGTACGATGTGTTTGCATAAGCGGTTACCACAGGCGCTACTCTCGTCGATAGC |
| #90-2-H3 | CGACTACTAATATTCAGCCGGCGCCGGTAGATAGCGAGGCTTTGGGGGTAGCTTTAAGTG |
| #90-2-H4 | CGGTCTAGGCTCAGTTGACGATACTTACTTAGGCAGGGTTACAACCCTTATGATGGGGTATGAGGC |
| #90-2-H5 | ACGTGGCCATTCATCCGGACCCGATGCTGTCGTGCTTCTCGTTGGCAATAGCGC |
| #90-3-H1 | GCGCTATTGCCAACGAGAAGCACGACA |
| #90-3-H2 | GGATTAGTACAGGTGACTAGTTCAGCTGTTGTTCGGATTCCAAGTAAGCTCGCATAGAGCTGGA |
| #90-3-H3 | CTTCTCGGAACGGTCCTGACGCATTCCTGCATCAATACGCGGCACCGGGGGTCC |
| #90-3-H4 | GATAGCATCTCGCCTTAGATCCGGCGGGGATACTTGGTCAAAGCTCACTACGGGACT |
| #90-3-H5 | AGAGTGGCTAGTGCAGATGCGCAGCGCAGATATGCTATACGAGATGAGCTTCAAATTCAT |
| #90-4-H1 | ATGAATTTGAAGCTCATCTCGTATAGCATATCT |
| #90-4-H2 | GGAGTTATGACGATATAACGCTAGGATCTGACGCGGTGACACCGGTCGTGTGACAACTGG |
| #90-4-H3 | GCTTTAAGTGAGGCATCAGAAGTATACTTTTAATGGTGCCGCTCCCAAATCCCCGATCTT |
| #90-4-H4 | GCCACGATTGCCTAAGCCGTCATGTTAGAGGCGGTCACAGCAAACCCCAGTTTACCG |
| #90-4-H5 | GTTCGATGATTATACGATGCCGGAGCGAACGACTACGCTCGAAGTTTGGTTATCTAGAGCACGT |
| #90-P1-1F | GCAAGTCACAGGAGTCCTCAC |
| #90-P1-1R | GTGAGGACTCCTGTG |
| #90-P1-2F | CACTGTCCAAGGAGTCGCTAG |
| #90-P1-2R | CTAGCGACTCCTTGG |
| #90-P2-1F | TGGTGTACGCTCTGAAGACCC |
| #90-P2-1R | GGGTCTTCAGAGCGT |
| #90-P2-2F | TGCGGCCGAGATAGAAGACAG |
| #90-P2-2R | CTGTCTTCTATCTCG |
| #90-P3-1F | TGCAGTACGGGTCTCCCTGCT |
| #90-P3-1R | AGCAGGGAGACCCGT |
| #90-P3-2F | TGCGGCCGAGGTCTCCTCGTG |
| #90-P3-2R | CACGAGGAGACCTCG |
| #90-P1-1FP | CACAGGAGTCCTCAC |
| #4180 | CAGTTTTCCTGGATTATGCCTGGCACCATTAAAGAAAATATCATCTTTGGTGTTTCCTATGATGAATATAGATACAGAAGC |
| #4181 | CAGTTTTCCTGGATTATGCCTGGCACCATTAAAGAAAATATgATCTTTGGTGTTTCCTATGATGAATATAGATACAGAAGC |
| #4182 | CAGTTTTCCTGGATTATGCCTGGCACCATTAAAGAAAATATCATCTgTGGTGTTTCCTATGATGAATATAGATACAGAAGC |
| #4183 | CAGTTTTCCTGGATTATGCCTGGCACCATTAAAGAAAATATCA---TTGGTGTTTCCTATGATGAATATAGATACAGAAGC |

REFERENCES CITED

Patent Documents

Evans, G. "Method for the complete chemical synthesis and assembly of genes and genomes". U.S. Pat. No. 6,521,427

Evans, G. "Method for assembly of a polynucleotide encoding a target polypeptide". U.S. Pat. No. 6,670,127

Gao, X., Zhou, X., and Gulari, E. "Method and Apparatus for Chemical and Biochemical Reactions Using Photo-Generated Reagents". U.S. Pat. No. 6,426,184

Gao, X. et al. "Linkers and co-coupling agents for optimization of oligonucleotide synthesis and purification on solid supports". US Patent Application 20030120035.

Mulligan, J. T., and Tabone, J. C. "Methods for improving the sequence fidelity of synthetic double-stranded oligonucleotides". U.S. Pat. No. 6,664,112

Zhou, X. et al. "Fluidic methods and devices for parallel chemical reactions". US Patent Application 20020012616.

Zhou, X., and Gulari, E. "Fluidic methods and devices for parallel chemical reactions". US Patent Application 20030118486.

Other References

Au, L.-C., Yang, F.-Y., Yang, W.-J., Lo, S.-H., and Kao, C.-F. (1998) Gene synthesis by a LCR-based approach: High-level production of leptin-L54 using synthetic gene in *Escherichia coli*. *Biochem. Biophys. Res. Commun.* 248, 200-203

Barnard, R., Futo, V., Pecheniuk, N., Slattery, M., and Walsh, T. (1998) PCR bias toward the wild-type k-ras and p53 sequences: implications for PCR detection of mutations and cancer diagnosis. *Biotechniques* 25, 684-691.

Bibikova, M. et al. (2004) Quantitative gene expression profiling in formalin-fixed, paraffin-embedded tissues using universal bead arrays. *Am. J. Pathol.* 165, 1799-1807

Cello J, et al. (2002) Chemical synthesis of poliovirus cDNA: generation of infectious virus in the absence of natural template. *Science* 297, 1016-1018

Dillon, P. J., and Rosen, C. A. (1990) A rapid method for the construction of synthetic genes using the polymerase chain reaction. *Biotechniques* 9, 298-300

Fan, J. B. et al. (2004) A versatile assay for high-throughput gene expression profiling on universal array matrices. *Genome Res.* 14, 878-885

Gao, X. and Han, X. (2001) Sequence specific recognition of ligand-DNA complexes studied by NMR. *Cur. Med. Chem. Review.* 8, 551-579

Gao, X., LeProust, E., Zhang, H., Srivannavit, O., Gulari, E., Yu, P., Nishiguchi, C., Xiang, Q., Zhou, X. (2001) Flexible DNA chip synthesis gated by deprotection using solution photogenerated acids. *Nucleic Acids Res.* 29, 4744-4750.

Gao, X., Gulari, E., and Zhou, X. (2004) In situ synthesis of oligonucleotide microarrays. *Biopolymers.* 73, 579-596.

Gao, X., Pellois, J. P., Kim, K., Na, Y., Gulari, E., and Zhou, X. (2004) High density peptide microarrays. In situ synthesis and applications. *Molecular Diversity.* 8, 177-187.

Gao, X., Yu, P. Y., LeProust, E., Sonigo, L., Pellois, J. P., and Zhang, H. (1998) Oligonucleotide synthesis using solution photogenerated acids. *J Am. Chem. Soc.* 120, 12698-12699.

Hanes, J., and Pluckthun, A. (1997) In vitro selection and evolution of functional proteins by using ribosome display. *Proc. Natl. Acad. Sci. USA* 94, 4937-4942.

Landegren U, Kaiser R, Sanders J, Hood L. (1988) A ligase-mediated gene detection technique. *Science* 241, 1077-1080.

Leproust, E., Zhang, H., Yu, P., Zhou, X., Gao, X. (2001) Characterization of oligodeoxyribonucleotide synthesis on glass plates. Nucleic Acids Res. 29, 2171-2180.

McBride, L. J., and Caruthers, M. H. (1983) An investigation of several deoxynucleotide phosphoramidites. *Tetrahedron Let.* 24, 245-248

Nickerson, D. A. et al. (1990) Automated DNA diagnostics using an ELISA-based oligonucleotide ligation assay. *Proc. Natl. Acad. Sci. USA* 87, 8923-8927

Odegrip, R. et al. (2004) CIS display: In vitro selection of peptides from libraries of protein-DNA complexes. *Proc. Natl. Acad Sci. USA* 101, 2806-2810.

Srivannavit, O. et al. (2004) Design and fabrication of microwell array chips for a solution-based, photogenerated acid-catalyzed parallel oligonuclotide DNA synthesis. *Sensors and Actuators A.* 116, 150-160.

Paddison, P. J., Cleary, M., Silval, J. M., Chang, K., Sheth, N., Sachidanandam, R., and Hannon, G. J. (2004) Cloning of short hairpin RNAs for gene knockdown. Nature Methods 1, 163-167.

Pellois, J. P., Zhou, X., Srivannavit, O., Zhou, T., Gulari, E., and Gao, X. (2002) Individually addressable parallel peptide synthesis on microchips. *Nat. Biotechnol.* 20, 922-926.

Roberts, R. W., and Szostak, J. W. (1997) RNA-peptide fusions for the in vitro selection of peptides and proteins. *Proc. Natl. Acad Sci. USA* 94, 12287-12302.

Rouillard J. M. et al. (2003) Gene2Oligo: oligonucleotide design for in vitro gene synthesis. *Nucleic Acids Res.* 32, W176-180

Saiki, R. K., Scharf, S., Faloona, F., Mullis, K. B., Horn, G. T., Erlich, H. A., Arnheim, N. (1985) Enzymatic amplification of beta-globin genomic sequences and restriction site analysis for diagnosis of sickle cell anemia. *Science* 230, 1350-1354.

Sarkar, T., Conwell, C. C., Harvey, L. C., Santai, C. T., Hud, N. V. (2005) Condensation of oligonucleotides assembled into nicked and gapped duplexes: potential structures for oligonucleotide delivery. *Nucleic Acids Res.* 33, 1 143-1151.

Smith, J., and Modrich, P. (1997) Removal of polymerase-produced mutant sequences from PCR products. *Proc. Natl. Acad Sci. USA* 94, 6847-6850.

Smith, O. H., Hutchison, C. A., Pfannkoch, C., and Venter, J. C. (2003) Generating a synthetic genome by whole genome assembly: X174 bacteriophage from synthetic oligonucleotides. *Proc. Natl. Acad. Sci. USA* 100, 15440-15445

Stemmer, W. P. (1994) Rapid evolution of a protein in vitro by DNA shuffling. *Nature* 370, 389-391.

Stemmer, W. P. C., et al. (1995) Single-step assembly of a gene and entire plasmid from large numbers of oligodeoxyribonucleotides. *Gene* 164, 49-53

Tian, J., Gong, H., Sheng, N., Zhou, X., Gulari, E., Gao, X., and Church, G. (2004) Accurate multiplex gene synthesis from programmable DNA chips. *Nature* 432, 1050-1054.

Vester, B., and Wengel, J. (2004) LNA (Locked Nucleic Acid): High-Affinity Targeting of Complementary RNA and DNA. *Biochemisty* 43, 13233-13241.

Zhong, X. B. et al. (2003) Single-nucleotide polymorphism genotyping on optical thin-film biosensor chips. *Proc. Natl. Acad. Sci. USA* 100, 11559-11564

Zhou, X. et al. (2004) Microfluidic picoarray synthesis of oligodeoxynucleotides and simultaneously assembling of multiple DNA sequences. *Nucleic Acids, Res.* 32, 5409-5417

We claim:

1. A method for simultaneously producing two full-length duplex nucleic acid polymers which have identical sequences on a solid surface comprising multiple sites wherein each of the two full-length duplex nucleic acid polymers is located on a different site on the solid surface and wherein each duplex consists of a first strand and a second complementary strand each strand having a 5' end and a 3' end comprising:

(a) placing a first capture probe of a defined length which is identical to a portion of the 3' end of the first strand on a first site on the solid surface;
(b) placing a second capture probe of a defined length which is identical to a portion of the 3' end of the second strand on a second site on the solid surface;
(c) contacting the solid surface with a pool of partially double-stranded oligonucleotides, which comprise overlapping fragments of the full length duplex nucleic acid polymers to be produced;
(d) hybridizing the first and second capture probes with the pool of partially double-stranded oligonucleotides such that first and second full-length duplex nucleic acid polymers are formed in which there are nicks and gaps in the duplexes;
(e) washing the first and second full-length duplex nucleic acid polymers under conditions to remove nucleic acid polymers which do not have sequences which are identical to the two full-length duplex nucleic acid polymers; and
(f) ligating and extending the first gapped and unligated full-length duplex nucleic acid and the second gapped and unligated full-length duplex nucleic acid to produce two full-length duplex nucleic acid polymers which have identical sequences wherein the first full-length duplex nucleic acid polymer is attached to the first site through the 3' end of the first strand and the second full-length duplex nucleic acid polymer is attached to the second site through the 3' end of the second strand.

2. The method of claim 1 wherein the placing of the first and second capture probes is accomplished by synthesizing the probes de nova on the solid surface.

3. The method of claim 1 wherein the first capture probe has a length of between about 6 to about 100 nucleotides and the second capture probe has a length of between about 6 to about 100 nucleotides.

* * * * *

SEQUENCE LISTING

<160> NUMBER OF SEQ ID NOS: 72

<210> SEQ ID NO 1
<211> LENGTH: 28
<212> TYPE: DNA
<213> ORGANISM: Homo sapiens

<400> SEQUENCE: 1
cagttttcca aaagctatcc gtaccatt                                      28

<210> SEQ ID NO 2
<211> LENGTH: 31
<212> TYPE: DNA

-continued

<210> ORGANISM: Homo sapiens

<400> SEQUENCE: 2 cagttttcc gaatgcagtc ctggcaccat t                              31

<210> SEQ ID NO 3
<211> LENGTH: 30
<212> TYPE: DNA
<213> ORGANISM: Homo sapiens

<400> SEQUENCE: 3
cagttttccc acgaagaacc tggcaccatt                               30

<210> SEQ ID NO 4
<211> LENGTH: 51
<212> TYPE: DNA
<213> ORGANISM: Homo sapiens

<400> SEQUENCE: 4
tgcgaaaata tcatcgaagg ttgctcctat gctgaatata gatacagaag c       51

<210> SEQ ID NO 5
<211> LENGTH: 51
<212> TYPE: DNA
<213> ORGANISM: Homo sapiens

<400> SEQUENCE: 5
aaagaaaata tcatcccgcc gcgttccgac gatgaatata gatacagaag c       51

<210> SEQ ID NO 6
<211> LENGTH: 51
<212> TYPE: DNA
<213> ORGANISM: Homo sapiens

<400> SEQUENCE: 6
cctgaaaata tcatctgcgg tcacgaatcc tatcgtgaat atagaagaag c       51

<210> SEQ ID NO 7
<211> LENGTH: 1000
<212> TYPE: DNA
<213> ORGANISM: Homo sapiens

<400> SEQUENCE: 7
ggtctttgtc acctccgtca atttgtatta gaaccgtgaa ggcccaagta acaggcccag    60
ggttaacatg tacggaacat actccttcca cggaagattg gggatgaaag ttgatacccca  120 aacttcatta acacaaaggc gatgtgggcc gagtactgtg cttacaccaa cagggcggct   180
caactgggtt ggtagccagc actagcttat tcacaattaa ggccgtatgc attctactgc   240
ttatccggtg gtgattgcag ccagggcgga agtgaacacg cttgtacgat gtgtttgcat   300
aagcggttac cacaggcgct actctcgtcg atagccgact actaatattc agccggcgcc   360
ggtagatagc gaggctttgg gggtagcttt aagtgcggtc taggctcagt tgacgatact   420
tacttaggca gggttacaac ccttatgatg gggtatgagg cacgtggcca ttcatccgga   480
cccgatgctg tcgtgcttct cgttggcaat agcgcggatt agtacaggtg actagttcag   540
ctgttgttcg gattccaagt aagctcgcat agagctggac ttctcggaac ggtcctgacg   600
cattcctgca tcaatacgcg gcaccggggg tccgatagca tctcgcctta gatccggcgg   660
gggatacttg gtcaaagctc actacgggac tagagtggct agtgcagatg cgcagcgcag   720
atatgctata cgagatgagc ttcaaattca tggagttatg acgatataac gctaggatct   780

```
gacgcggtga caccggtcgt gtgacaactg ggctttaagt gaggtctcag aagtatactt    840
ttaatggtgc cgctcccaaa tccccgatct tgccacgatt gcctaagccg tcatgttaga    900
ggcggtcaca gcaaaccccc agtttaccgg ttcgatgatt atacgatgcc ggagcgaacg    960
actacgctcg aagtttggtt atctagagca cgtccgtcta                         1000

<210> SEQ ID NO 8
<211> LENGTH: 274
<212> TYPE: DNA
<213> ORGANISM: Homo sapiens

<400> SEQUENCE: 8
ggtctttgtc acctccgtca atttgtatta gaaccgtgaa ggcccaagta acaggcccag     60
ggttaacatg tacggaacat actccttcca cggaagattg gggatgaaag ttgataccca    120
aacttcatta acacaaaggc gatgtgggcc gagtactgtg cttacaccaa cagggcggct    180
caactgggtt ggtagccagc actagcttat tcacaattaa ggccgtatgc attctactgc    240
ttatccggtg gtgattgcag ccagggcgga agtg                                274

<210> SEQ ID NO 9
<211> LENGTH: 241
<212> TYPE: DNA
<213> ORGANISM: Homo sapiens

<400> SEQUENCE: 9
aacacgcttg tacgatgtgt ttgcataagc ggttaccaca ggcgctactc tcgtcgatag     60
ccgactacta atattcagcc ggcgccggta gatagcgagg ctttgggggt agctttaagt    120
gcggtctagc ctcagttgac gatacttact taggcagggt tacaaccctt atgatggggt    180
atgaggcacg tggccattca tccggacccg atgctgtcgt gcttctcgtt ggcaatagcg    240
c                                                                    241

<210> SEQ ID NO 10
<211> LENGTH: 236
<212> TYPE: DNA
<213> ORGANISM: Homo sapiens

<400> SEQUENCE: 10
ggattagtac aggtgactag ttcagctgtt gttcggattc caagtaagct cgcatagagc     60
tggacttctc ggaacggtcc tgacgcattc ctgcatcaat acgcggcacc ggggtccga    120 tagcatctcg ccttagatcc ggcggggat acttggtcaa agctcactac gggactagag    180
tggctagtgc agatgcgcag cgcagatatg ctatacgaga tgagcttcaa attcat       236

<210> SEQ ID NO 11
<211> LENGTH: 249
<212> TYPE: DNA
<213> ORGANISM: Homo sapiens

<400> SEQUENCE: 11
ggagttatga cgatataacg ctaggatctg acgcggtgac accggtcgtg tgacaactgg     60
gctttaagtg aggtctcaga agtatacttt taatggtgcc gctcccaaat ccccgatctt    120
gccacgattg cctaagccgt catgttagag gcggtcacag caaaccccca gtttaccggt    180
tcgatgatta tacgatgccg gagcgaacga ctacgctcga agtttggtta tctagagcac    240
gtccgtcta                                                            249
```

```
<210> SEQ ID NO 12
<211> LENGTH: 1000
<212> TYPE: DNA
<213> ORGANISM: Homo sapiens

<400> SEQUENCE: 12
tagacggacg tgctctagat aaccaaactt cgagcgtagt cgttcgctcc ggcatcgtat      60
aatcatcgaa ccggtaaact gggggttttgc tgtgaccgcc tctaacatga cggcttaggc     120
aatcgtggca agatcgggga tttgggagcg gcaccattaa aagtatactt ctgagacctc     180
acttaaagcc cagttgtcac acgaccggtg tcaccgcgtc agatcctagc gttatatcgt     240
cataactcca tgaatttgaa gctcatctcg tatagcatat ctgcgctgcg catctgcact     300
agccactcta gtcccgtagt gagctttgac caagtatccc ccgccggatc taaggcgaga     360
tgctatcgga cccccggtgc cgcgtattga tgcaggaatg cgtcaggacc gttccgagaa     420
gtccagctct atgcgagctt acttggaatc cgaacaacag ctgaactagt cacctgtact     480
aatccgcgct attgccaacg agaagcacga cagcatcggg tccggatgaa tggccacgtg     540
cctcataccc catcataagg gttgtaaccc tgcctaagta agtatcgtca actgagccta     600
gaccgcactt aaagctaccc ccaaagcctc gctatctacc ggcgccggct gaatattagt     660
agtcggctat cgacgagagt agcgcctgtg gtaaccgctt atgcaaacac atcgtacaag     720
cgtgttcact tccgccctgg ctgcaatcac caccggataa gcagtagaat gcatacggcc     780
ttaattgtga ataagctagt gctggctacc aacccagttg agccgccctg ttggtgtaag     840
cacagtactc ggcccacatc gcctttgtgt taatgaagtt tgggtatcaa ctttcatccc     900
caatcttccg tggaaggagt atgttccgta catgttaacc ctgggcctgt tacttgggcc     960
ttcacggttc taatacaaat tgacggaggt gacaaagacc                          1000

<210> SEQ ID NO 13
<211> LENGTH: 274
<212> TYPE: DNA
<213> ORGANISM: Homo sapiens

<400> SEQUENCE: 13
cacttccgcc ctggctgcaa tcaccaccgg ataagcagta gaatgcatac ggccttaatt      60
gtgaataagc tagtgctggc taccaaccca gttgagccgc cctgttggtg taagcacagt     120
actcggccca catcgccttt gtgttaatga agtttgggta tcaactttca tccccaatct     180
tccgtggaag gagtatgttc cgtacatgtt aaccctgggc tgttacttg ggccttcacg     240 gttctaatac aaattgacgg aggtgacaaa gacc                                 274

<210> SEQ ID NO 14
<211> LENGTH: 241
<212> TYPE: DNA
<213> ORGANISM: Homo sapiens

<400> SEQUENCE: 14
gcgctattgc caacgagaag cacgacagca tcgggtccgg atgaatggcc acgtgcctca      60
taccccatca taagggttgt aaccctgcct aagtaagtat cgtcaactga gcctagaccg     120
cacttaaagc tacccccaaa gcctcgctat ctaccgcgcg cggctgaata ttagtagtcg     180
gctatcgacg agagtagcgc ctgtggtaac cgcttatgca aacacatcgt acaagcgtgt     240
t                                                                     241
```

```
<210> SEQ ID NO 15
<211> LENGTH: 236
<212> TYPE: DNA
<213> ORGANISM: Homo sapiens

<400> SEQUENCE: 15
atgaatttga agctcatctc gtatagcata tctgcgctgc gcatctgcac tagccactct     60
agtcccgtag tgagctttga ccaagtatcc cccgccggat ctaaggcgag atgctatcgg    120 accccggtg ccgcgtattg atgcaggaat gcgtcaggac cgttccgaga agtccagctc     180
tatgcgagct tacttggaat ccgaacaaca gctgaactag tcacctgtac taatcc        236

<210> SEQ ID NO 16
<211> LENGTH: 249
<212> TYPE: DNA
<213> ORGANISM: Homo sapiens

<400> SEQUENCE: 16
tagacggacg tgctctagat aaccaaactt cgagcgtagt cgttcgctcc ggcatcgtat     60
aatcatcgaa ccggtaaact gggggtttgc tgtgaccgcc tctaacatga cggcttaggc    120
aatcgtggca agatcgggga tttgggagcg gcaccattaa aagtatactt ctgagacctc    180
acttaaagcc cagttgtcac acgaccggtg tcaccgcgtc agatcctagc gttatatcgt    240
cataactcc                                                            249

<210> SEQ ID NO 17
<211> LENGTH: 60
<212> TYPE: DNA
<213> ORGANISM: Homo sapiens

<400> SEQUENCE: 17
ggtctttgtc acctccgtca atttgtatta gaaccgtgaa ggcccaagta acaggcccag     60

<210> SEQ ID NO 18
<211> LENGTH: 66
<212> TYPE: DNA
<213> ORGANISM: Homo sapiens

<400> SEQUENCE: 18
ggttaacatg tacggaacat actccttcca cggaagattg gggatgaaag ttgatacccca    60 aacttc                                                                66

<210> SEQ ID NO 19
<211> LENGTH: 58
<212> TYPE: DNA
<213> ORGANISM: Homo sapiens

<400> SEQUENCE: 19
attaacacaa aggcgatgtg ggccgagtac tgtgcttaca ccaacagggc ggctcaac       58

<210> SEQ ID NO 20
<211> LENGTH: 63
<212> TYPE: DNA
<213> ORGANISM: Homo sapiens

<400> SEQUENCE: 20
tgggttggta gccagcacta gcttattcac aattaaggcc gtatgcattc tactgcttat     60
ccg                                                                   63
```

<210> SEQ ID NO 21
<211> LENGTH: 27
<212> TYPE: DNA
<213> ORGANISM: Homo sapiens

<400> SEQUENCE: 21
gtggtgattg cagccagggc ggaagtg                                27

<210> SEQ ID NO 22
<211> LENGTH: 59
<212> TYPE: DNA
<213> ORGANISM: Homo sapiens

<400> SEQUENCE: 22
gtggtgattg cagccagggc ggaagtgaac acgcttgtac gatgtgtttg cataagcgg    59

<210> SEQ ID NO 23
<211> LENGTH: 56
<212> TYPE: DNA
<213> ORGANISM: Homo sapiens

<400> SEQUENCE: 23
ttaccacagg cgctactctc gtcgatagcc gactactaat attcagccgg cgccgg       56

<210> SEQ ID NO 24
<211> LENGTH: 66
<212> TYPE: DNA
<213> ORGANISM: Homo sapiens

<400> SEQUENCE: 24
tagatagcga ggctttgggg gtagctttaa gtgcggtcta ggctcagttg acgatactta   60
cttagg                                                             66

<210> SEQ ID NO 25
<211> LENGTH: 60
<212> TYPE: DNA
<213> ORGANISM: Homo sapiens

<400> SEQUENCE: 25
cagggttaca accctatga tggggtatga ggcacgtggc cattcatccg gacccgatgc    60

<210> SEQ ID NO 26
<211> LENGTH: 27
<212> TYPE: DNA
<213> ORGANISM: Homo sapiens

<400> SEQUENCE: 26
tgtcgtgctt ctcgttggca atagcgc                                      27

<210> SEQ ID NO 27
<211> LENGTH: 60
<212> TYPE: DNA
<213> ORGANISM: Homo sapiens

<400> SEQUENCE: 27
tgtcgtgctt ctcgttggca atagcgcgga ttagtacagg tgactagttc agctgttgtt   60

<210> SEQ ID NO 28
<211> LENGTH: 58
<212> TYPE: DNA
<213> ORGANISM: Homo sapiens -continued

<400> SEQUENCE: 28
cggattccaa gtaagctcgc atagagctgg acttctcgga acggtcctga cgcattcc    58

<210> SEQ ID NO 29
<211> LENGTH: 54
<212> TYPE: DNA
<213> ORGANISM: Homo sapiens

<400> SEQUENCE: 29
tgcatcaata cgcggcaccg ggggtccgat agcatctcgc cttagatccg gcgg    54

<210> SEQ ID NO 30
<211> LENGTH: 58
<212> TYPE: DNA
<213> ORGANISM: Homo sapiens

<400> SEQUENCE: 30
gggatacttg gtcaaagctc actacgggac tagagtggct agtgcagatg cgcagcgc    58

<210> SEQ ID NO 31
<211> LENGTH: 33
<212> TYPE: DNA
<213> ORGANISM: Homo sapiens

<400> SEQUENCE: 31
agatatgcta tacgagatga gcttcaaatt cat    33

<210> SEQ ID NO 32
<211> LENGTH: 66
<212> TYPE: DNA
<213> ORGANISM: Homo sapiens

<400> SEQUENCE: 32
agatatgcta tacgagatga gcttcaaatt catggagtta tgacgatata acgctaggat    60
ctgacg    66

<210> SEQ ID NO 33
<211> LENGTH: 60
<212> TYPE: DNA
<213> ORGANISM: Homo sapiens

<400> SEQUENCE: 33
cggtgacacc ggtcgtgtga caactgggct ttaagtgagg catcagaagt atacttttaa    60

<210> SEQ ID NO 34
<211> LENGTH: 58
<212> TYPE: DNA
<213> ORGANISM: Homo sapiens

<400> SEQUENCE: 34
tggtgccgct cccaaatccc cgatcttgcc acgattgcct aagccgtcat gttagagg    58

<210> SEQ ID NO 35
<211> LENGTH: 58
<212> TYPE: DNA
<213> ORGANISM: Homo sapiens

<400> SEQUENCE: 35
cggtcacagc aaaccccag tttaccggtt cgatgattat acgatgccgg agcgaacg    58

<210> SEQ ID NO 36
<211> LENGTH: 33

```
<212> TYPE: DNA
<213> ORGANISM: Homo sapiens

<400> SEQUENCE: 36
actacgctcg aagtttggtt atctagagca cgt                              33

<210> SEQ ID NO 37
<211> LENGTH: 33
<212> TYPE: DNA
<213> ORGANISM: Homo sapiens

<400> SEQUENCE: 37
ttctaataca aattgacgga ggtgacaaag acc                              33

<210> SEQ ID NO 38
<211> LENGTH: 60
<212> TYPE: DNA
<213> ORGANISM: Homo sapiens

<400> SEQUENCE: 38
ccgtgaaggc ccaagtaaca ggcccagggt taacatgtac ggaacatact ccttccacgg   60

<210> SEQ ID NO 39
<211> LENGTH: 64
<212> TYPE: DNA
<213> ORGANISM: Homo sapiens

<400> SEQUENCE: 39
aagattgggg atgaaagttg atacccaaac ttcattaaca caaaggcgat gtgggccgag   60
tact                                                             64

<210> SEQ ID NO 40
<211> LENGTH: 57
<212> TYPE: DNA
<213> ORGANISM: Homo sapiens

<400> SEQUENCE: 40
gtgcttacac caacagggcg gctcaactgg gttggtagcc agcactagct tattcac      57

<210> SEQ ID NO 41
<211> LENGTH: 60
<212> TYPE: DNA
<213> ORGANISM: Homo sapiens

<400> SEQUENCE: 41
aattaaggcc gtatgcattc tactgcttat ccggtggtga ttgcagccag ggcggaagtg   60

<210> SEQ ID NO 42
<211> LENGTH: 27
<212> TYPE: DNA
<213> ORGANISM: Homo sapiens

<400> SEQUENCE: 42
cacttccgcc ctggctgcaa tcaccac                                     27

<210> SEQ ID NO 43
<211> LENGTH: 61
<212> TYPE: DNA
<213> ORGANISM: Homo sapiens

<400> SEQUENCE: 43
aacacgcttg tacgatgtgt ttgcataagc ggttaccaca ggcgctactc tcgtcgatag   60
```

```
c                                                              61

<210> SEQ ID NO 44
<211> LENGTH: 60
<212> TYPE: DNA
<213> ORGANISM: Homo sapiens

<400> SEQUENCE: 44
cgactactaa tattcagccg gcgccggtag atagcgaggc tttgggggta gctttaagtg      60

<210> SEQ ID NO 45
<211> LENGTH: 66
<212> TYPE: DNA
<213> ORGANISM: Homo sapiens

<400> SEQUENCE: 45
cggtctaggc tcagttgacg atacttactt aggcagggtt acaacccta tgatggggta      60 tgaggc                                                              66

<210> SEQ ID NO 46
<211> LENGTH: 54
<212> TYPE: DNA
<213> ORGANISM: Homo sapiens

<400> SEQUENCE: 46
acgtggccat tcatccggac ccgatgctgt cgtgcttctc gttggcaata gcgc           54

<210> SEQ ID NO 47
<211> LENGTH: 27
<212> TYPE: DNA
<213> ORGANISM: Homo sapiens

<400> SEQUENCE: 47
gcgctattgc caacgagaag cacgaca                                         27

<210> SEQ ID NO 48
<211> LENGTH: 64
<212> TYPE: DNA
<213> ORGANISM: Homo sapiens

<400> SEQUENCE: 48
ggattagtac aggtgactag ttcagctgtt gttcggattc caagtaagct cgcatagagc      60
tgga                                                                64

<210> SEQ ID NO 49
<211> LENGTH: 54
<212> TYPE: DNA
<213> ORGANISM: Homo sapiens

<400> SEQUENCE: 49
cttctcggaa cggtcctgac gcattcctgc atcaatacgc ggcaccgggg gtcc           54

<210> SEQ ID NO 50
<211> LENGTH: 58
<212> TYPE: DNA
<213> ORGANISM: Homo sapiens

<400> SEQUENCE: 50
gatagcatct cgccttagat ccggcggggg atacttggtc aaagctcact acgggact       58

<210> SEQ ID NO 51
<211> LENGTH: 60
```

-continued

<210> SEQ ID NO 51
<211> LENGTH: (not shown)
<212> TYPE: DNA
<213> ORGANISM: Homo sapiens

<400> SEQUENCE: 51
agagtggcta gtgcagatgc gcagcgcaga tatgctatac gagatgagct tcaaattcat    60

<210> SEQ ID NO 52
<211> LENGTH: 33
<212> TYPE: DNA
<213> ORGANISM: Homo sapiens

<400> SEQUENCE: 52
atgaatttga agctcatctc gtatagcata tct                                 33

<210> SEQ ID NO 53
<211> LENGTH: 60
<212> TYPE: DNA
<213> ORGANISM: Homo sapiens

<400> SEQUENCE: 53
ggagttatga cgatataacg ctaggatctg acgcggtgac accggtcgtg tgacaactgg    60

<210> SEQ ID NO 54
<211> LENGTH: 60
<212> TYPE: DNA
<213> ORGANISM: Homo sapiens

<400> SEQUENCE: 54
gctttaagtg aggcatcaga agtatacttt taatggtgcc gctcccaaat ccccgatctt    60

<210> SEQ ID NO 55
<211> LENGTH: 58
<212> TYPE: DNA
<213> ORGANISM: Homo sapiens

<400> SEQUENCE: 55
gccacgattg cctaagccgt catgttagag gcggtcacag caaaccccca gtttaccg      58

<210> SEQ ID NO 56
<211> LENGTH: 64
<212> TYPE: DNA
<213> ORGANISM: Homo sapiens

<400> SEQUENCE: 56
gttcgatgat tatacgatgc cggagcgaac gactacgctc gaagtttggt tatctagagc    60
acgt                                                                 64

<210> SEQ ID NO 57
<211> LENGTH: 21
<212> TYPE: DNA
<213> ORGANISM: Homo sapiens

<400> SEQUENCE: 57
gcaagtcaca ggagtcctca c                                              21

<210> SEQ ID NO 58
<211> LENGTH: 15
<212> TYPE: DNA
<213> ORGANISM: Homo sapiens

<400> SEQUENCE: 58
gtgaggactc ctgtg                                                     15

```
<210> SEQ ID NO 59
<211> LENGTH: 21
<212> TYPE: DNA
<213> ORGANISM: Homo sapiens

<400> SEQUENCE: 59
cactgtccaa ggagtcgcta g                                              21

<210> SEQ ID NO 60
<211> LENGTH: 15
<212> TYPE: DNA
<213> ORGANISM: Homo sapiens

<400> SEQUENCE: 60
ctagcgactc cttgg                                                     15

<210> SEQ ID NO 61
<211> LENGTH: 21
<212> TYPE: DNA
<213> ORGANISM: Homo sapiens

<400> SEQUENCE: 61
tggtgtacgc tctgaagacc c                                              21

<210> SEQ ID NO 62
<211> LENGTH: 15
<212> TYPE: DNA
<213> ORGANISM: Homo sapiens

<400> SEQUENCE: 62
gggtcttcag agcgt                                                     15

<210> SEQ ID NO 63
<211> LENGTH: 21
<212> TYPE: DNA
<213> ORGANISM: Homo sapiens

<400> SEQUENCE: 63
tgcggccgag atagaagaca g                                              21

<210> SEQ ID NO 64
<211> LENGTH: 15
<212> TYPE: DNA
<213> ORGANISM: Homo sapiens

<400> SEQUENCE: 64
ctgtcttcta tctcg                                                     15

<210> SEQ ID NO 65
<211> LENGTH: 21
<212> TYPE: DNA
<213> ORGANISM: Homo sapiens

<400> SEQUENCE: 65
tgcagtacgg gtctccctgc t                                              21

<210> SEQ ID NO 66
<211> LENGTH: 15
<212> TYPE: DNA
<213> ORGANISM: Homo sapiens

<400> SEQUENCE: 66
agcagggaga cccgt                                                     15
```

```
<210> SEQ ID NO 67
<211> LENGTH: 21
<212> TYPE: DNA
<213> ORGANISM: Homo sapiens

<400> SEQUENCE: 67
tgcggccgag gtctcctcgt g                                              21

<210> SEQ ID NO 68
<211> LENGTH: 15
<212> TYPE: DNA
<213> ORGANISM: Homo sapiens

<400> SEQUENCE: 68
cacgaggaga cctcg                                                     15

<210> SEQ ID NO 69
<211> LENGTH: 81
<212> TYPE: DNA
<213> ORGANISM: Homo sapiens

<400> SEQUENCE: 69
cagttttcct ggattatgcc tggcaccatt aaagaaaata tcatctttgg tgtttcctat    60
gatgaatata gatacagaag c                                              81

<210> SEQ ID NO 70
<211> LENGTH: 81
<212> TYPE: DNA
<213> ORGANISM: Homo sapiens

<400> SEQUENCE: 70
cagttttcct ggattatgcc tggcaccatt aaagaaaata tgatctttgg tgtttcctat    60
gatgaatata gatacagaag c                                              81

<210> SEQ ID NO 71
<211> LENGTH: 81
<212> TYPE: DNA
<213> ORGANISM: Homo sapiens

<400> SEQUENCE: 71
cagttttcct ggattatgcc tggcaccatt aaagaaaata tcatctgtgg tgtttcctat    60
gatgaatata gatacagaag c                                              81

<210> SEQ ID NO 72
<211> LENGTH: 78
<212> TYPE: DNA
<213> ORGANISM: Homo sapiens

<400> SEQUENCE: 72
cagttttcct ggattatgcc tggcaccatt aaagaaaata tcattggtgt ttcctatgat    60
gaatatagat acagaagc                                                  78
```